US009006686B2

(12) United States Patent
Wada

(10) Patent No.: US 9,006,686 B2
(45) Date of Patent: Apr. 14, 2015

(54) SURFACE PLASMON RESONANCE FLUORESCENCE ANALYSIS DEVICE AND SURFACE PLASMON RESONANCE FLUORESCENCE ANALYSIS METHOD

(75) Inventor: Shigeru Wada, Kishiwada (JP)

(73) Assignee: Konica Minolta Holdings, Inc. (JP)

( * ) Notice: Subject to any disclaimer, the term of this patent is extended or adjusted under 35 U.S.C. 154(b) by 175 days.

(21) Appl. No.: 13/824,809

(22) PCT Filed: Sep. 26, 2011

(86) PCT No.: PCT/JP2011/005362
§ 371 (c)(1),
(2), (4) Date: Mar. 18, 2013

(87) PCT Pub. No.: WO2012/042805
PCT Pub. Date: Apr. 5, 2012

(65) Prior Publication Data
US 2013/0175457 A1 Jul. 11, 2013

(30) Foreign Application Priority Data

Sep. 30, 2010 (JP) ................................. 2010-221506

(51) Int. Cl.
*G01N 21/64* (2006.01)
(52) U.S. Cl.
CPC .............. *G01N 21/64* (2013.01); *G01N 21/648* (2013.01)
(58) Field of Classification Search
CPC ............................. G01N 21/64; G01N 21/648
USPC ............................................ 250/458.1, 459.1
See application file for complete search history.

(56) References Cited

U.S. PATENT DOCUMENTS

| 5,064,619 A | 11/1991 | Finlan |
| 2004/0201849 A1 | 10/2004 | Codner et al. |
| 2005/0012932 A1 | 1/2005 | Yamada et al. |
| 2005/0062974 A1 | 3/2005 | Ivarsson |
| 2006/0187459 A1 | 8/2006 | Ok et al. |

FOREIGN PATENT DOCUMENTS

| JP | 63-82346 A | 4/1988 |
| JP | 2-103469 A | 4/1990 |

(Continued)

OTHER PUBLICATIONS

International Search Report for International Application No. PCT/JP2011/005362, mailed Nov. 1, 2011, with English translation.

(Continued)

*Primary Examiner* — Mark R Gaworecki
(74) *Attorney, Agent, or Firm* — Cantor Colburn LLP

(57) ABSTRACT

In the present invention, a specimen is made to flow on a metal film on a prism, and excitation light ($\alpha$) is emitted in a predetermined direction. By changing the position of a reflective member that reflects the excitation light ($\alpha$), and adjusting the orientation of a reflective surface of the reflective member, the incident angle ($\theta$) is changed while maintaining a state in which the excitation light ($\alpha$) that enters the prism is reflected at a specific position on the metal film. The intensity of light to be generated on the metal film is measured, and the reflective member is positioned to match the position of the reflective member and the orientation of the reflective surface when a maximum amount of light is measured.

15 Claims, 10 Drawing Sheets

(56) References Cited

FOREIGN PATENT DOCUMENTS

| | | |
|---|---|---|
| JP | 2004-527741 A | 9/2004 |
| JP | 2004-354092 A | 12/2004 |
| JP | 2006-201163 A | 8/2006 |
| JP | 2009-204484 A | 9/2009 |
| JP | 2010091553 A | 4/2010 |

OTHER PUBLICATIONS

Japanese Office Action corresponding to Application No. 2012-536190; Date of Mailing: Jan. 6, 2015, with English translation.

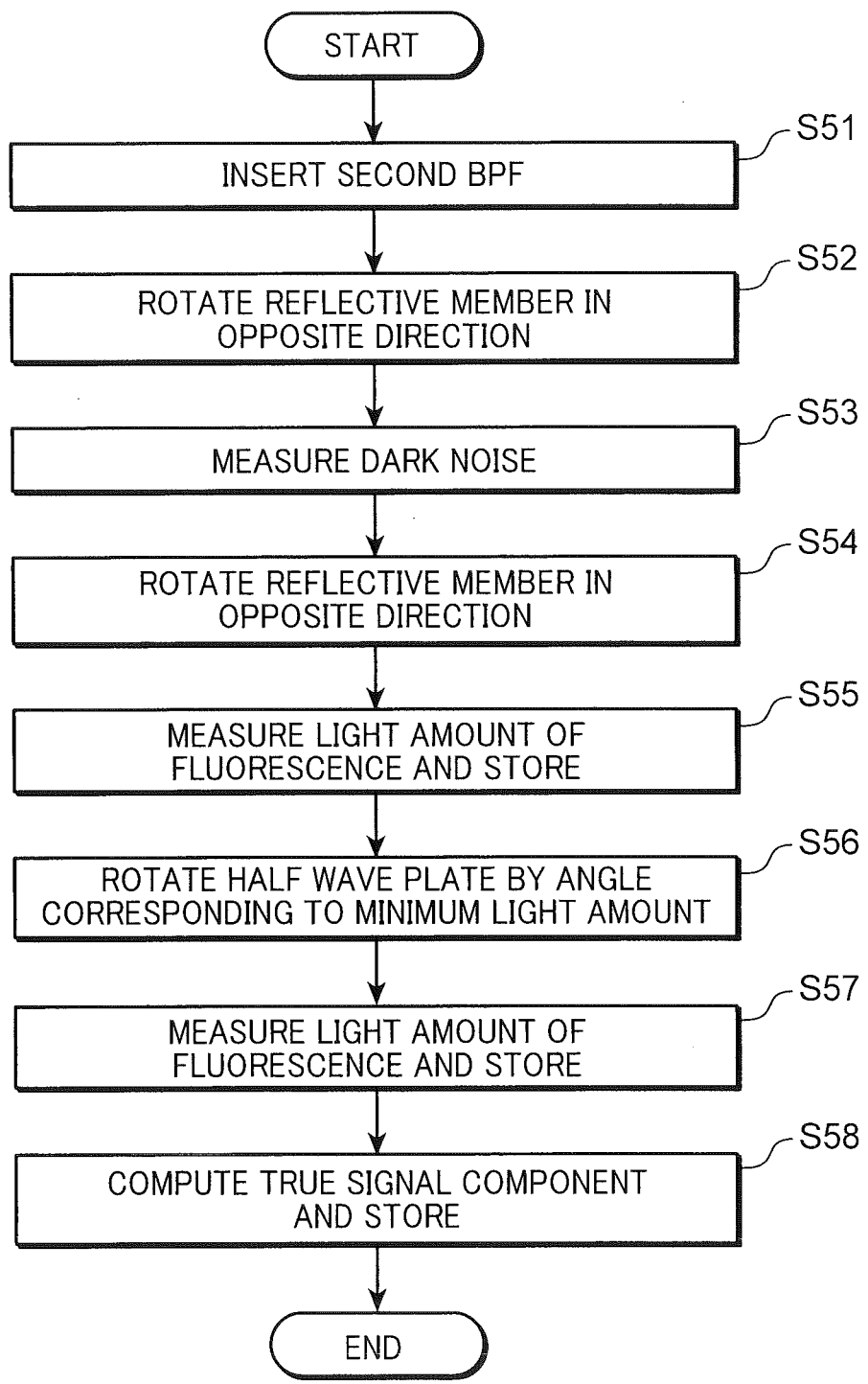

SURFACE PLASMON RESONANCE FLUORESCENCE ANALYSIS DEVICE AND SURFACE PLASMON RESONANCE FLUORESCENCE ANALYSIS METHOD

CROSS REFERENCE TO RELATED APPLICATIONS

This is the U.S. national stage of application No. PCT/JP2011/005362, filed on 26 Sep. 2011. Priority under 35 U.S.C. §119(a) and 35 U.S.C. §365(b) is claimed from Japanese Application No. 2010-221506, filed 30 Sep. 2010, the disclosure of which is also incorporated herein by reference.

TECHNICAL FIELD

The present invention relates to a surface plasmon resonance fluorescence analysis device and a surface plasmon resonance fluorescence analysis method configured to detect a specimen contained in a sample solution, utilizing surface plasmon resonance (SPR).

BACKGROUND ART

Conventionally, in biomeasurement for detecting proteins or DNAs, there has been known a surface plasmon resonance fluorescence analysis method (Surface Plasmon-field enhanced Fluorescence Spectroscopy: SPFS), as a method for detecting a specimen (material to be detected) with high sensitivity.

According to SPFS, a prism having a metal film made of e.g. gold or silver formed on a predetermined surface thereof is prepared, excitation light is caused to enter the metal film from the side of the prism in such a manner that the predetermined surface is subjected to total reflection, and light (evanescent wave) emerging from the metal film in reflecting the excitation light on the metal film is utilized. Specifically, according to SPFS, when the metal film is subjected to total reflection of excitation light, a specimen that is contained in a sample solution and flows over the surface of the metal film, or a fluorescent material (labeling material) labeled on the specimen is excited by an evanescent wave emerging from the metal film, and fluorescence (excitation fluorescence) emitted from the specimen or from the fluorescent material is analyzed. By performing the analysis as described above, it is possible to detect the presence of the specimen or to detect the quantity of the specimen.

In an optical measurement utilizing SPFS, it is necessary to set an excitation light incident angle (specifically, an incident angle of excitation light with respect to a metal film) in accordance with individual prisms or conditions of reaction fields for sufficiently enhancing the electric field near the surface of the metal film by surface plasmon resonance. In view of the above, in the optical measurement utilizing SPFS, generally, a regression measurement system utilizing light resulting from an electric field (enhanced electric field) which is enhanced near the surface of the metal film is configured for adjusting the incident angle of excitation light with respect to the metal film. In such an optical measurement, excitation light is caused to enter the prism with a small angle with respect to the metal film so that the excitation light enters while undergoing total reflection in the interface between the metal film and the prism. As a result of the above operation, the reflection position (irradiation position) of excitation light on the reflection film is likely to displace, resulting from slight displacement of the incident angle of the excitation light with respect to the metal film. Further, the reflection position may displace afterwards due to a temperature change in a measurement environment. Since the region of electric field enhanced by surface plasmon resonance is narrow, such displacement of the reflection position of excitation light may result in lowering the precision in measuring light resulting from the enhanced electric field.

In view of the above, as disclosed in patent literature 1, there has been developed an apparatus, wherein the entirety of an excitation optical system is made to swing by a link mechanism in such a manner that the reflection position (irradiation position) of excitation light on a metal film formed on a prism coincides with a center of rotation, whereby the incident angle of excitation light is made to be adjustable. With use of the apparatus, swinging the entirety of the excitation optical system about the reflection position as a center of rotation makes it possible to adjust the irradiation direction of excitation light of the excitation optical system for securing an incident angle that enables to obtain an enhanced electric field suitable for detecting a specimen, while suppressing displacement of the reflection position.

Further, as disclosed in patent literature 2, there has been developed an apparatus, wherein multiple excitation lights having different incident angles are simultaneously irradiated at a reflection position (irradiation position) of excitation light on a metal film. With use of the apparatus, one of the excitation lights has an incident angle suitable for individual prisms or for individual conditions of reaction fields. Thus, it is possible to obtain an enhanced electric field suitable for detecting a specimen without causing displacement of the reflection position.

However, in the former apparatus, since the entirety of the excitation optical system provided with a light source and lenses is made to swing by a link mechanism, the excitation optical system is likely to vibrate due to the weight thereof. Further, since the link mechanism is constituted of many components, the reflection position of excitation light on a metal film may displace, resulting from backlash of each of the components.

Further, in the latter apparatus, it is possible to suppress displacement of the reflection position, because scanning of the incident angle of excitation light with respect to a metal film is not performed by a mechanism or a like device. However, self fluorescence is generated in the course of propagation of excitation light that does not contribute to surface plasmon resonance on the metal film through a prism. Then, in measuring fluorescence generated by excitation of a fluorescent material labeled on a specimen in an enhanced electric field, the self fluorescence of excitation light that does not contribute to surface plasmon resonance is also measured. This may lower the S/N ratio of a signal to be obtained by the measurement.

CITATION LIST

Patent Literature

Patent literature 1: JP 2004-354092A
Patent literature 2: JP 2009-204484A

SUMMARY OF INVENTION

In view of the above, an object of the invention is to provide, in an analysis device utilizing SPFS, a surface plasmon resonance fluorescence analysis device and a surface plasmon resonance fluorescence analysis method that enable to suppress displacement of the reflection position of excitation light on a metal film, while suppressing lowering of the S/N ratio of a signal to be obtained by measuring light resulting from an enhanced electric field that is generated near the metal film on a prism.

A surface plasmon resonance fluorescence analysis device and a surface plasmon resonance fluorescence analysis method according to the invention perform positioning of a reflective member to match the position of the reflective member and the orientation of a reflective surface of the reflective member when the amount of light that is generated on the side of a metal film opposite from the side of a prism is maximized, in the case where the incident angle of excitation light with respect to the metal film is changed by adjusting the reflective member, while maintaining a state in which the excitation light is reflected at a specific position on the metal film. According to the invention, it is possible to provide a surface plasmon resonance fluorescence analysis device and a surface plasmon resonance fluorescence analysis method that enable to suppress displacement of the reflection position of excitation light on the metal film, while suppressing lowering of the S/N ratio of a signal to be obtained by measuring light resulting from an enhanced electric field that is generated near the metal film on the prism.

These and other objects, features and advantages of the present invention will become more apparent upon reading the following detailed description along with the accompanying drawings.

BRIEF DESCRIPTION OF DRAWINGS

FIG. 9 is a flowchart showing an excitation fluorescence measuring sequence in FIG. 5;

DESCRIPTION OF EMBODIMENTS

In the following, an embodiment of the invention is described referring to the accompanying drawings.

A surface plasmon resonance fluorescence analysis device (hereinafter, also simply called an "analysis device") according to the embodiment is configured to excite a fluorescent material labeled on a material to be detected (hereinafter, also simply called a "specimen"), utilizing an evanescent wave (enhanced electric field) emerging from a reflection interface of a prism, in the case where excitation light entered to the prism is reflected on the reflection interface, while undergoing total reflection on the reflection interface. The analysis device is configured to detect the specimen by detecting the light amount of fluorescence generated by excitation of the fluorescent material.

Figure 1:
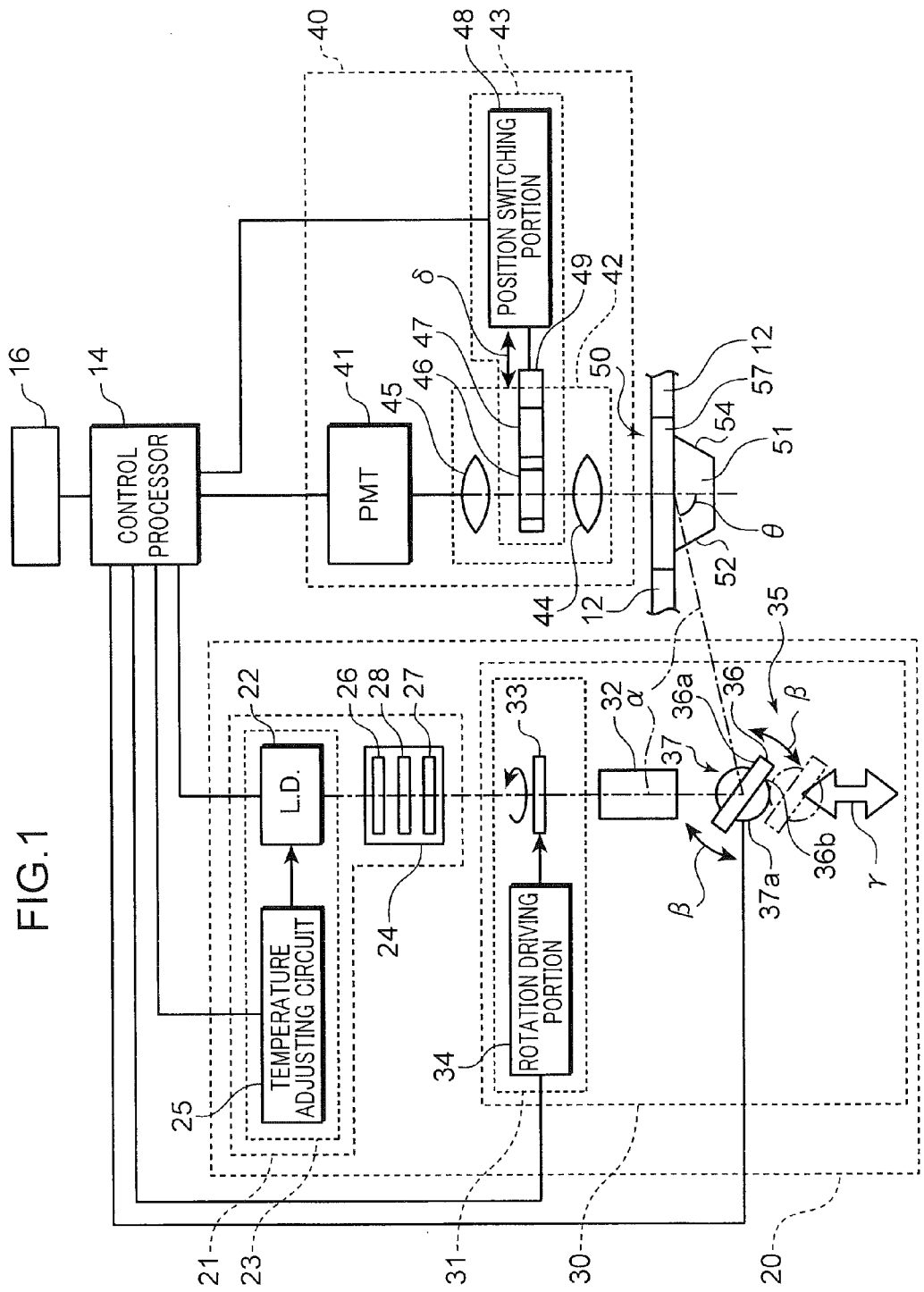
FIG. 1 is a functional block diagram showing a configuration of a surface plasmon resonance fluorescence analysis device according to the invention in a state that an analysis chip is set.

As shown in FIG. 1, the analysis device is provided with a chip holding portion 12 for holding an analysis chip 50; an excitation light emitting portion 20 for outputting excitation light onto the analysis chip 50 held on the chip holding portion 12; a light measuring portion 40 for measuring the intensity of light generated on the analysis chip 50; a control processor 14 (control portion) for controlling the respective constituent elements of the analysis device 10 such as the chip holding portion 12, the excitation light emitting portion 20, and the light measuring portion 40, and for performing various computations; and a display portion 16 for displaying various information such as computation results. The analysis device 10 is further provided with a pretreatment portion (not shown) for performing pretreatment of a blood sample from a patient. In the pretreatment portion, a sample solution is prepared by receiving a reagent chip (not shown) and by performing pretreatment (e.g. blood cell separation, dilution, mixing) of a blood sample injected to the reagent chip, and the sample solution is injected to the analysis chip 50. The reagent chip is formed with a number of storage units. A reagent, a diluent, a cleaning solution and the like are individually packed in the storage units, in addition to a blood sample.

Figure 2:
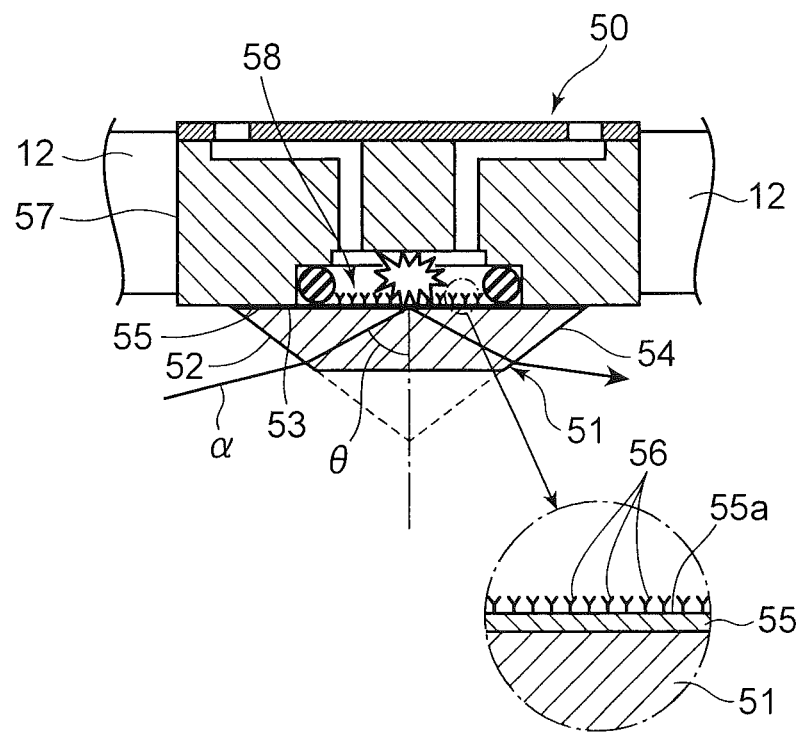
FIG. 2 is an enlarged view of a chip holding portion of the surface plasmon resonance fluorescence analysis device, and a configuration of an analysis chip held on the chip holding portion.

As also shown in FIG. 2, the analysis chip 50 is provided with a prism 51, a metal film 55 formed on a surface of the prism 51, and a channel member 57 for forming a channel 58 along which a sample solution containing a specimen and a cleaning liquid are allowed to flow on the metal film 55 in contact with the metal film 55. Analysis chips 50 in the embodiment are replaced one after another, each time a specimen is detected (analyzed).

The prism 51 includes, in the surfaces thereof, an incident surface 52 for allowing incidence of excitation light α from the excitation light emitting portion 20 into the prism 51, a deposition surface (predetermined surface) 53 having the metal film 55 formed thereon for reflecting the excitation light α entered to the prism 51, and an emission surface 54 from which the excitation light α reflected on the metal film 55 is outputted to the outside of the prism 51. The prism 51 is made of a transparent glass or resin. The emission surface 54 is a surface on which the excitation light α impinges for the first time after being reflected on the metal film 55. The emission surface 54 is formed on an optical surface of the prism in the same manner as the incident surface 52, so that light of the S-wave component of the excitation light α reflected on the metal film 55 does not stay in the prism 51. The prism 51 in the embodiment is made of a transparent resin having a refractive index of from about 1.4 to 1.6. The prism 51 may be made of glass. Further alternatively, the prism 51 may have such a shape that the incident surface 52, the deposition surface 53, and the emission surface 54 are included in the surfaces of the prism 51. In other words, the prism 51 may be of any shape, as far as the excitation light α entered from the incident surface 52 into the prism 51 is subjected to total reflection on the metal film 55 formed on the deposition surface 53, and the excitation light α (more specifically, the S-wave component of the excitation light α) is outputted from the emission surface 54 without randomly reflecting and staying in the prism 51.

The metal film 55 is a thin metal film deposited (formed) on the deposition surface 53 of the prism 51. The metal film 55 in the embodiment is made of gold. The metal film 55 is configured to amplify an evanescent wave (enhanced electric field), which is generated by causing the excitation light α to enter to the prism 51 while undergoing total reflection on the deposition surface 53, and by reflecting the entered excitation light α at a position of the deposition surface 53 where the metal film 55 is formed. In other words, as compared with a configuration, in which an evanescent wave is generated by causing total reflection of excitation light α on a surface (deposition surface 53) devoid of a metal film 55, forming the metal film 55 on the deposition surface 53 and generating surface plasmon resonance on the metal film 55 is advantageous in amplifying the evanescent wave to be formed. Thus, an enhanced electric field is formed near a surface 55a of the metal film 55.

The material of the metal film 55 is not limited to gold, but may be any metal that causes surface plasmon resonance. For instance, the metal film 55 may be made of silver, copper, or aluminum (including an alloy thereof).

Further, capturing bodies 56 for capturing a specific antigen are immobilized on a surface 55a of the metal film 55 (surface opposite from the side of the prism 51). These capturing bodies 56 are immobilized on the surface 55a of the metal film 55 by surface treatment.

The channel member 57 is formed on the deposition surface 53 of the prism 51 (specifically, on the metal film 55), whereby the channel 58 along which a sample solution is allowed to flow is formed in cooperation with the deposition surface 53. The channel member 57 is made of a transparent resin. The channel member 57 is joined to the prism 51 by e.g. an adhesive agent, welding such as laser welding or ultrasonic welding, or clamping connection using a clamping member. The channel 58 has such a shape that the area where the metal film 55 is contacted with a sample solution is set larger than a measurement area by the light measuring portion 40.

After the thus-constructed analysis chip 50 is placed in the pretreatment portion of the analysis device 10, the sample solution subjected to pretreatment in the pretreatment portion is injected (supplied) to the channel 58. Then, after reaction of the capturing bodies 56 immobilized on the metal film 55 with the specimen (specific antigen) is finished, the analysis chip 50 carrying the sample solution is transported to the chip holding portion 12. Upon being transported to the chip holding portion 12, the analysis chip 50 is held on the chip holding portion 12 in a predetermined posture with respect to the analysis device 10.

The chip holding portion 12 holds the analysis chip 50 thereon in such a manner that the analysis chip 50 is set in a predetermined posture with respect to the analysis device 10 in detecting a specimen. The predetermined posture is a posture that the excitation light α emitted from the excitation light emitting portion 20 enters the prism 51 from the incident surface 52 while undergoing total reflection on the deposition surface 53, and the entered excitation light α is reflected on the metal film 55. Further, the chip holding portion 12 detachably holds the analysis chip 50. The chip holding portion 12 in the embodiment holds the analysis chip 50 thereon in such a manner that the prism 51 is located beneath the channel member 57.

In the analysis device 10, a light absorbent (not shown) is disposed near the emission surface 54 of the analysis chip 50 held on the chip holding portion 12 for keeping the light emitted from the emission surface 54 from being affected on the light measuring portion 40.

The excitation light emitting portion 20 is configured to cause the excitation light α to enter the prism 51 in such a manner that the excitation light α is reflected on the metal film 55 of the prism 51 included in the analysis chip 50 held on the chip holding portion 12. Specifically, the excitation light emitting portion 20 has a light source portion 21 for emitting linearly polarized excitation light, and an excitation optical system 30 for guiding the excitation light α emitted from the light source portion 21 to the incident surface 52 of the prism 51.

The light source portion 21 has a light source unit 23 including an excitation light source 22, and a first wave-shaping portion 24 for shaping the excitation light α emitted from the excitation light source 22. The light source portion 21 in the embodiment downwardly emits the excitation light α. The excitation light source 22 in the embodiment is a laser diode.

The light source unit 23 has the excitation light source 22, and a temperature adjusting circuit 25 for adjusting a temperature of the excitation light source 22. The light source unit 23 is configured to collimate the excitation light α emitted from the excitation light source 22, and to adjust and hold the posture of the excitation light source 22 in such a manner that the excitation light α enters the metal film 55 of the prism 51 from the minor axis side thereof. This is for the following reason.

Figure 3:
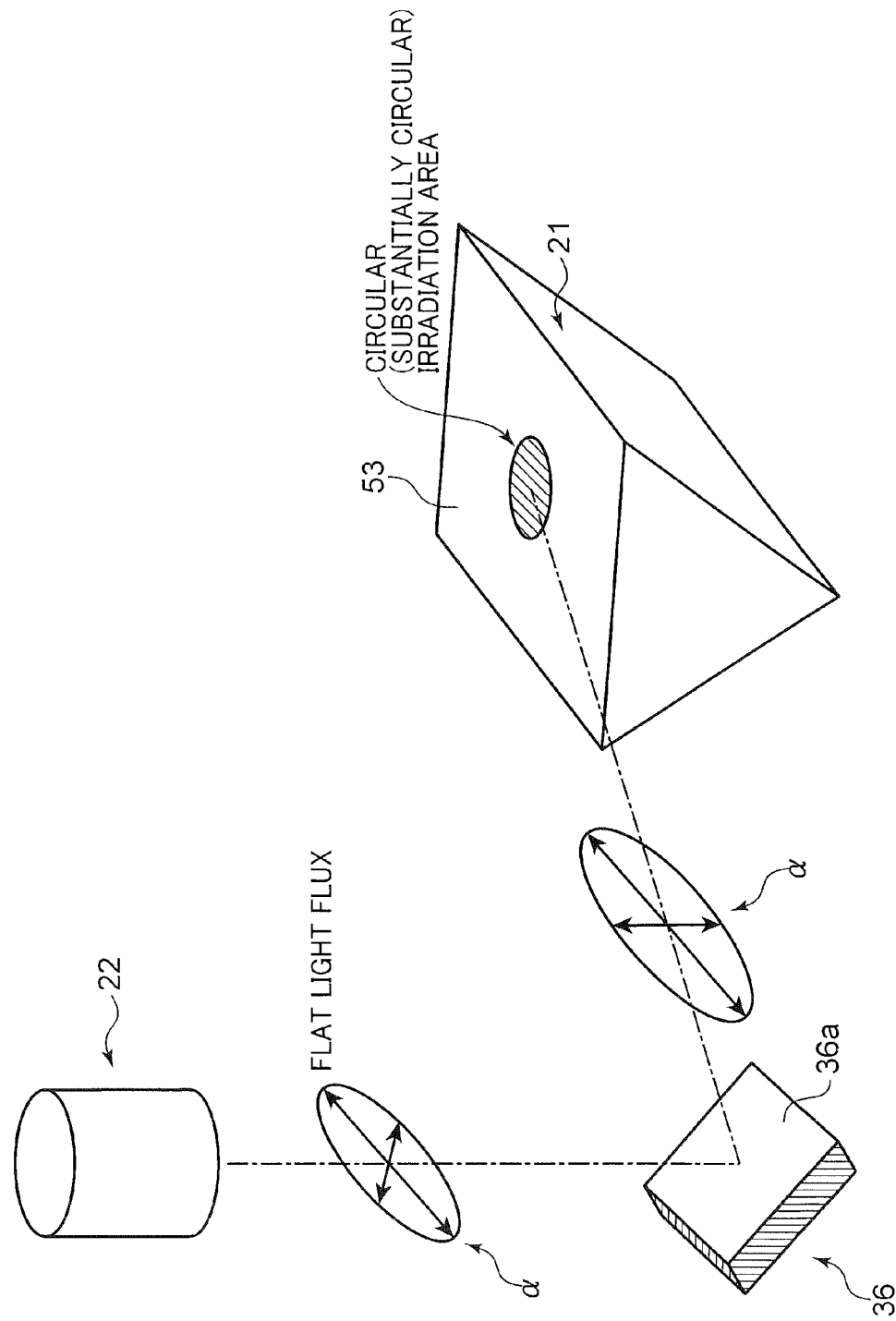
FIG. 3 is a diagram showing a polarization state of excitation light and an irradiation area of excitation light on a metal film in the surface plasmon resonance fluorescence analysis device.

The excitation light α emitted from the excitation light source (laser diode) 22, even after collimation, has a flat shape, and the polarization directions thereof are substantially polarized in a certain direction. Accordingly, in the case where the excitation light α enters the prism 51 while undergoing total reflection on the deposition surface 53 (with a small incident angle with respect to the deposition surface 53), by adjusting the posture of the excitation light source 22 and by retaining the posture after the adjustment, the contour of the irradiation area of the excitation light α on the deposition surface 53 has a substantially circular shape (see FIG. 3).

The temperature adjusting circuit 25 is a regression circuit for adjusting a temperature of the excitation light source (laser diode) 22. Specifically, the temperature adjusting circuit 25 monitors the light amount of light rays separated from light rays of excitation light α after collimation by e.g. a photodiode (not shown), whereby the temperature of the excitation light source 22 is adjusted to make the wavelength and the light amount of excitation light α to be emitted constant. The above operation is performed in view of a point that the wavelength and the emission energy of light to be emitted from the excitation light source 22 vary depending on temperatures.

The first wave shaping portion 24 shapes the excitation light α emitted from the light source unit 23 by multiple filters (optical filters) so that the excitation light α has an excitation wavelength, at which the polarization direction is uniquely defined. Specifically, the first wave shaping portion 24 has a first band-pass filter (hereinafter, simply called a "first BPF") 26, a linear polarization filter (hereinafter, simply called an "LPF") 27, and a first ND filter (hereinafter, simply called a "first NDF") 28. The firs BPF 26 filters the emission light from the excitation light source 22 into light of a narrow wavelength band including only a center wavelength component, in view of a point that the emission light has a slight wavelength distribution range. Further, the LPF 27 filters the emission light from the excitation light source 22 into linearly polarized light, in view of a point that the emission light has a slight difference in phase difference component. Further, the first NDF 28 is a so-called neutral density filter. Specifically, the first NDF 28 dims the light emitted from the excitation light source 22 to thereby adjust the light amount of the excitation light α to be emitted from the light source portion 21. It should be noted that the first NDF 28 may be omitted from the first wave shaping portion 24 depending on an intensity of emission light to be emitted from the excitation light source 22.

The excitation optical system 30 guides the excitation light α from the light source portion 21 to the prism 51 of the analysis chip 50 held on the chip holding portion 12. The excitation optical system 30 has a polarization direction adjusting portion 31 for changing the polarization direction of the excitation light α, a beam shaping optical system 32 for adjusting the contour or configuration of a beam of the excitation light α, and an incident path adjusting portion 35 for changing the incident path of the excitation light α into the prism 51 to thereby change the reflection position of the excitation light α on the metal film 55 or change an incident angle θ of the excitation light α with respect to the metal film 55.

The polarization direction adjusting portion 31 has a half wave plate 33, and a rotation driving portion 34 for rotating the half wave plate 33.

The half wave plate 33 is disposed on the optical path of the excitation optical system 30, and is used as a polarization rotator for continuously rotating the polarization direction of the excitation light α. The rotation driving portion 34 is configured to rotate the polarization direction of the excitation light α with respect to the metal film 55 by rotating the half wave plate 33. The rotation driving portion 34 in the embodiment has a stepping motor, and is configured to rotate the half wave plate 33 by driving the stepping motor based on an instruction signal from the control processor 14. Rotating the half wave plate 33 as described above causes rotation of the polarization direction of the excitation light α which is linearly polarized by the first wave shaping portion 24. By performing the above operation, the amount of the P-wave component and the amount of the S-wave component of the excitation light α to be entered to the metal film 55 change. In other words, causing the rotation driving portion 34 to rotate the half wave plate 33 makes it possible to freely change the polarization direction from a condition in which an evanescent wave is maximally emerged from the metal film 55 (i.e. a condition in which the degree of enhancing the electric field to be formed near the surface 55a of the metal film 55 is maximized) to a condition in which emergence of evanescent wave is completely cut off (i.e. a condition in which an enhanced electric field is not formed at all near the surface 55a of the metal film 55).

Figure 10B:
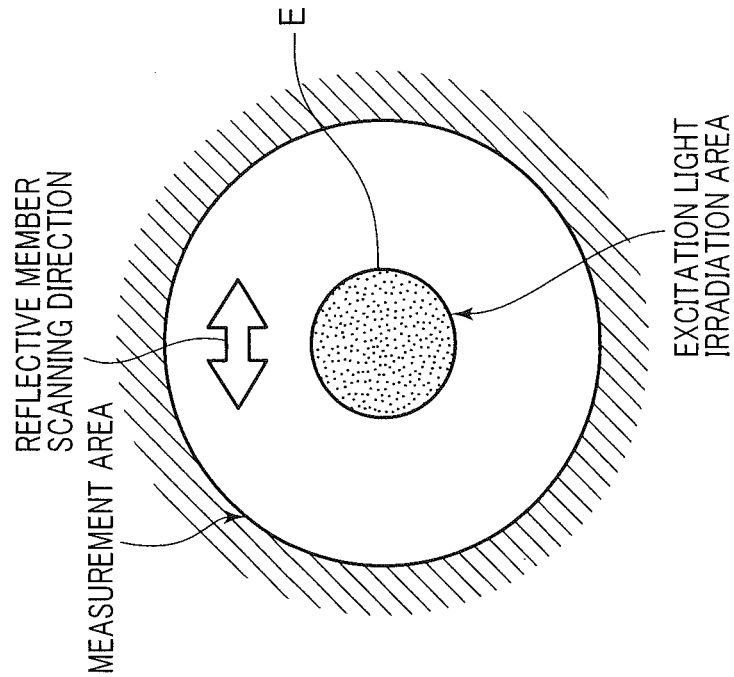
FIG. 10B is a diagram showing a state that the irradiation area is moved to a center position of a measurement area.

The beam shaping optical system 32 adjusts the beam size of the excitation light α or the contour or configuration of a beam, utilizing e.g. a slit or a zoom function so that the contour of the irradiation area of the excitation light α on the metal film 55 has a circular shape of a predetermined diameter. The irradiation area of the excitation light α on the metal film 55 in the embodiment is adjusted to be smaller than the measurement area by the light measuring portion 40 (see FIG. 10B). By performing the above adjustment, even if the irradiation area of the excitation light α on the metal film 55 is slightly displaced, it is possible to measure, by the light measuring portion 40, light resulting from surface plasmon resonance, and light resulting from an enhanced electric field based on the surface plasmon resonance.

The incident path adjusting portion 35 has a reflective member 36 for reflecting the excitation light α from the light source portion 21, and a reflective member driving portion (driving portion) 37 for driving the reflective member 36.

The reflective member 36 has a reflective surface 36a for reflecting the excitation light α thereon. The reflective member 36 in the embodiment is a reflection mirror. The reflective member 36 is constructed in such a manner that on the reflective surface 36a, there is deposited a dielectric multilayer film (specifically, a dielectric multilayer film in which both of the P-wave component and the S-wave component are deprived of wavelength dependence on the excitation light wavelength) in which phase displacement or dimming of light does not occur in excitation light α before incidence onto the reflective surface 36a, and in excitation light α after reflection on the reflective surface 36a. By forming the dielectric multilayer film as described above, detection precision and sensitivity of a specimen by the analysis device 10 are improved.

Further, a member made of a non-reflective light absorbing material capable of absorbing the excitation light α without reflecting the excitation light α is attached to a back surface 36b of the reflective member 36. Examples of the non-reflective light absorbing material include an absorption-type ND film and suede fabric.

The reflective member driving portion 37 has a stage 37a, a rotation driving mechanism (not shown) which is disposed on the stage 37a and which is configured to drive and rotate the reflective member 36 while supporting the reflective member 36, and a reciprocation driving mechanism (not shown) for reciprocally driving the stage 37a.

The rotation driving mechanism is configured to change the orientation of the reflective surface 36a by rotating the reflective member 36 (see the arrow β in FIG. 1). Specifically, the rotation driving mechanism supports the reflective member 36 in such a manner that the reflective surface 36a perpendicularly intersects a plane (the plane of FIG. 1) including the optical path of excitation light α to be entered to the reflective member 36, and the optical path of excitation light α after reflection on the reflective member 36. Then, the rotation driving mechanism rotates the reflective member 36 based on an instruction signal from the control processor 14 in such a manner that the reflective surface 36a rotates along the plane including the optical paths, while maintaining the perpendicular posture of the reflective member 36 (posture that the reflective surface 36a perpendicularly intersects the plane including the optical paths). The rotation driving mechanism has a rotation motor, and changes the orientation of the reflective surface 36a by directly or indirectly driving and rotating the reflective member 36 by the rotation motor. Further, the rotation driving mechanism may rotate the reflective member 36 to such a position that the excitation light α from the light source portion 21 enters the back surface 36b of the reflective member 36, based on an instruction signal from the control processor 14. In the embodiment, the reflective member 36 is mounted on the rotation driving mechanism at such a position that the centroid of the reflective member 36 passes near the center of rotation of the reflective member 36, and the rotation motor is configured to generate a sufficiently large torque. The rotation motor in the embodiment is a stepping motor having a high resolution. The rotation motor rotates the reflective member 36 at a predetermined angular interval (in other words, stepwise in the rotating direction), based on an instruction signal from the control processor 14. The predetermined interval is associated with the resolution for adjusting the orientation of the reflective surface 36a, and is set in accordance with the performance of the device, as necessary.

The reciprocation driving mechanism linearly moves the stage 37a i.e. the reflective member 36 along the optical axis of the excitation light α from the light source portion 21 (see the arrow γ in FIG. 1). The reciprocation driving mechanism in the embodiment reciprocally drives the stage 37a in the optical axis direction of the excitation light α from the light source portion 21, namely, in up and down directions. Specifically, the reciprocation driving mechanism is configured to control the stepping motor by an instruction signal from the control processor 14, and the stage 37a carrying the rotation driving mechanism and the reflective member 36 thereon is reciprocally moved up and down by a screw feeding mechanism to be driven by the stepping motor. In other words, the reciprocation driving mechanism moves the reflective member 36 to a predetermined position on the optical axis with high precision in accordance with an instruction signal from the control processor 14, while maintaining the orientation of the reflective surface 36a with respect to the optical axis of the excitation light α from the light source portion 21.

The light measuring portion 40 has a light receiving portion 41, a measurement optical system 42 for guiding light from the analysis chip 50 to the light receiving portion 41, and a second wave shaping portion 43 for shaping the light to be guided by the measurement optical system 42. Further, the light measuring portion 40 measures an intensity (in the embodiment, a light amount) of light to be generated on the metal film 55 of the analysis chip 50 and on a region adjacent to the metal film 55 (hereinafter, also simply called "light to be generated on the metal film 55").

The light receiving portion 41 is configured to receive light and to output an intensity signal indicative of a light amount of the received light. In the embodiment, a photomultiplier tube (PMT) having a high sensitivity and a high S/N ratio is used as the light receiving portion 41 for detecting weak light such as fluorescence to be generated by exciting a fluorescent material labeled on a specimen. The light receiving portion 41 is not limited to the PMT, but may be e.g. a cooling type CCD image sensor.

Figure 4:
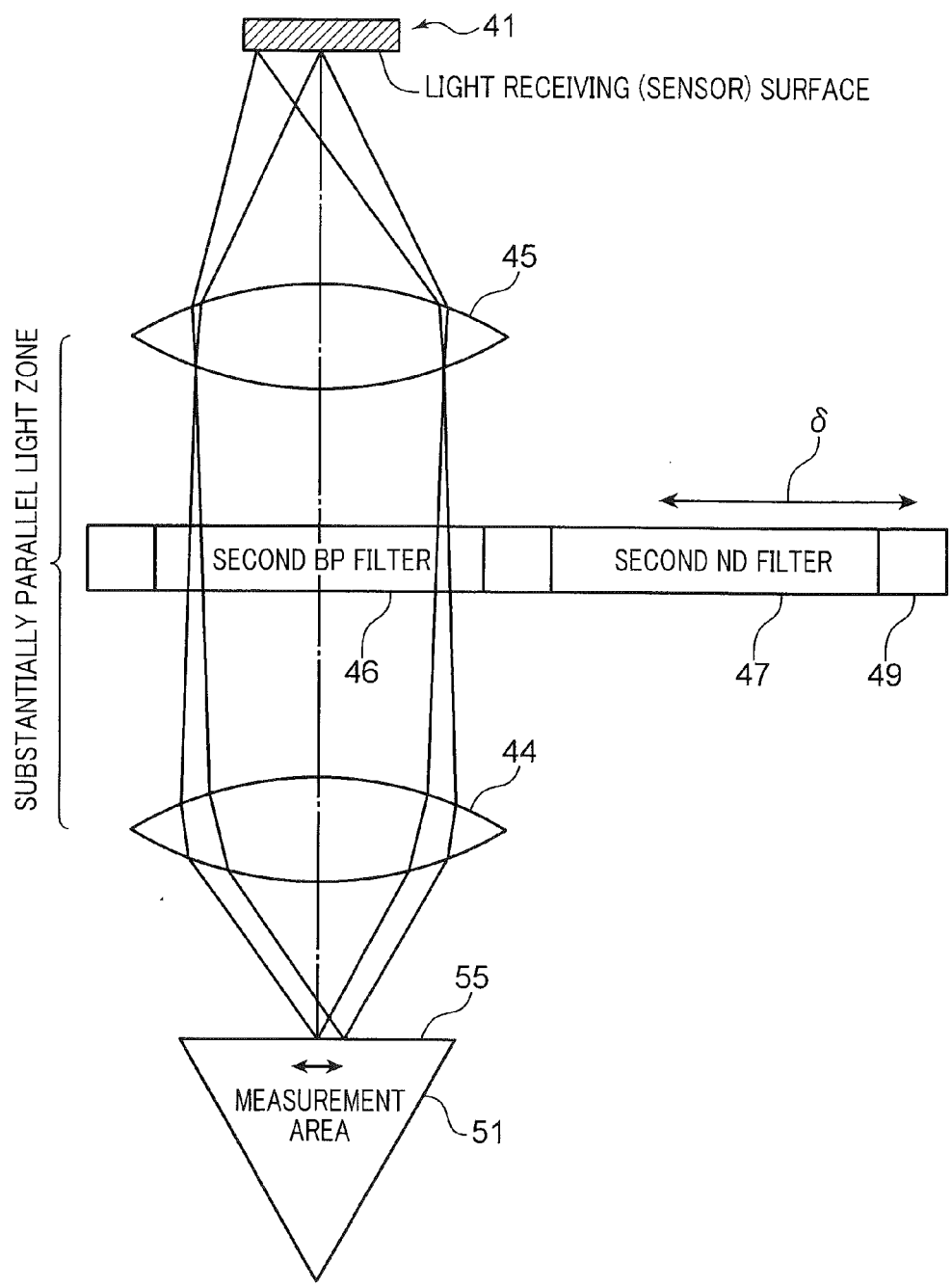
FIG. 4 is a diagram for describing a measurement optical system of the surface plasmon resonance fluorescence analysis device.

As also shown in FIG. 4, the measurement optical system 42 is a conjugation optical system that is less likely to be affected by stray light, and has a condensing lens 44 and an image forming lens 45. The measurement optical system 42 in the embodiment is a two-lens-group conjugation optical system configured in such a manner that light travelling between two lens groups i.e. between the condensing lens 44 and the image forming lens 45 becomes parallel light or substantially parallel light.

The second wave shaping portion 43 is configured to remove, from the light to be guided in the measurement optical system 42, an excitation light component (e.g. plasmon scattering light, Raman scattering light, or diffusion light) for adjusting the light amount (intensity) of light to be guided in the measurement optical system 42. The second wave shaping portion 43 has a second band-pass filter (first optical filter) 46, a second ND filter (second optical filter) 47, and a position switching portion 48 for switching the position of each of the filters 46 and 47.

The second band-pass filter (hereinafter, simply called a "second BPF") 46 cuts off light at a wavelength (excitation wavelength) of the excitation light α. By performing the cut-off operation as described above, the second BPF 46 is capable of preventing incidence of light (e.g. leak light from the excitation light emitting portion 20, plasmon scattering light, or diffusion light) at a wavelength other than the wavelength of fluorescence (light generated by excitation of a fluorescent material labeled on a specimen by an enhanced electric field) onto the light receiving portion 41. In other words, the second BPF 46 removes a noise component from the light to be entered to the light receiving portion 41 to thereby improve detection precision and sensitivity of weak fluorescence by the light receiving portion 41.

The second ND filter 47 (hereinafter, simply called a "second NDF") is a so-called neutral density filter, and is configured to emit light by attenuating the incident light. The second NDF 47 is capable of measuring e.g. plasmon scattering light by the light receiving portion (in the embodiment, PMT) 41 for detecting weak light (in the embodiment, fluorescence) by dimming e.g. plasmon scattering light or diffusion light to be guided in the measurement optical system 42. Specifically, the light amount of light to be measured for obtaining an incident angle θ1 of the excitation light α at which the enhanced electric field is maximized is significantly large, as compared with the light amount of excitation fluorescence to be measured in detecting a specimen. Accordingly, in the case where the common light receiving portion 41 is used, using the second NDF 47 for dimming the light to be measured so as to obtain the incident angle θ1 of the excitation light α at which the enhanced electric field is maximized is advantageous in preventing damage of the light receiving portion 41.

The second BPF 46 and the second NDF 47 are held on a common holding frame 49 in such a manner that the filters 46 and 47 are aligned on a certain plane substantially perpendicular to the optical axis (specifically, a plane substantially orthogonal to the optical axis of light travelling through the measurement optical system 42).

The position switching portion 48 is configured to switch the position of each of the second BPF 46 and the second NDF 47 between a filtering position and a retracted position.

The filtering position is a position on the optical path of the measurement optical system 42. Specifically, the filtering position is a position at which each of the second BPF 46 and the second NDF 47 perpendicularly intersects the optical axis of parallel light or substantially parallel light between the condensing lens 44 and the image forming lens 45, and crosses the parallel light or the substantially parallel light, between the condensing lens 44 and the image forming lens 45. By defining the filtering position as described above, the analysis device 10 is operable to precisely detect a specimen. In other words, if the second BPF 46 or the second NDF 47 is inclined with respect to the optical axis of e.g. parallel light travelling between the condensing lens 44 and the image forming lens 45, the optical axis of light passing through the second BPF 46 or through the second NDF 47 is shifted. This may lower the measurement precision by the light measuring portion 40.

On the other hand, the retracted position is a position deviated from the optical path of the measurement optical system 42.

The position switching portion 48 switches the position of each of the second BPF 46 and the second NDF 47 in such a manner that when the second BPF 46 is in the filtering position, the second NDF 47 is set to the retracted position (see FIG. 4), and when the second BPF 46 is in the retracted position, the second NDF 47 is set to the filtering position. The position switching portion 48 in the embodiment is configured to switch the position of each of the second BPF 46 and the second NDF 47 by reciprocally moving the holding frame 49 along a plane on which the filters 46 and 47 are aligned (see the arrow 6 in FIG. 4). By performing the switching operation as described above, the operations of switching the positions of the two filters 46 and 47 are simultaneously performed by one drive source.

The position switching portion 48 performs the operation of switching the position of each of the filters 46 and 47 in accordance with an instruction signal from the control processor 14.

The second wave shaping portion 43 in the embodiment is provided with the second BPF 46 and the second NDF 47. The invention is not limited to the above. As far as the light amount of light to be measured does not exceed an allowable light amount of the light receiving portion 41, the second NDF 47 may be omitted from the second wave shaping portion 43. Further, the second NDF 47 may also be omitted, in the case where the analysis device has a configuration of switching between light receiving portions depending on light to be measured, specifically, in the case where the analysis device has a configuration of switching between a light receiving portion 41 for receiving fluorescence, and another light receiving portion for receiving light having a larger light amount than the light amount of fluorescence.

Further, in the embodiment, the operation of switching the position of each of the filters 46 and 47 is performed by reciprocally moving the holding frame 49 by the position switching portion 48. The invention is not limited to the above. For instance, a disc-shaped holding frame may individually holds the second BPF 46 and the second NDF 47 in such a manner that the filters 46 and 47 are aligned on one plane, and a position switching portion may rotate the disc-shaped holding frame about an intermediate position between the second BPF 46 and the second NDF 47 as a center of rotation. In the above modified configuration, it is also possible to switch the position of each of the filters 46 and 47. Further alternatively, a position switching portion may have two drive sources, so that switching of the position of the second BPF 46 and switching of the position of the second NDF 47 are individually carried out by the two drive sources.

The control processor 14 controls each of the constituent elements constituting the analysis device 10. For instance, in the case where the analysis device 10 analyzes a specimen, the control processor 14 controls the light source portion 21, the polarization direction adjusting portion 31, the incident path adjusting portion 35, and the light measuring portion 40. By performing the above controls, the analysis device 10 is operable to perform e.g. a resonance angle scanning process, an optimum position scanning process, a birefringence measuring process, and an excitation fluorescence measuring process. Further, in the case where a specimen is analyzed, the control processor 14 is operable to perform computations based on an output signal to be transmitted from the light measuring portion 40 (specifically, the light receiving portion 41) for analyzing fluorescence measured by the light measuring portion 40. For instance, the control processor 14 counts the number of fluorescent particles per unit area detected by the light measuring portion 40, and calculates an increase of fluorescence with time. A computation result by the control processor 14 is outputted to the display portion 16 which is connected to the control processor 14. The details on concrete control operations and computations by the control processor 14 are described later.

The display portion 16 displays a computation result by the control processor 14, based on an output signal from the control processor 14. The display portion 16 may be a liquid crystal display which is configured to display a computation result on a screen, or may be a printer which is configured to print out a computation result. Further alternatively, the display portion 16 may be a combination of a device for displaying a screen and a device for printing out a computation result.

In the following, analysis of a specimen to be performed by the analysis device 10 having the aforementioned configuration is described also referring to FIGS. 5 through 9. The details on a control operation of each of the constituent elements of the analysis device 10 by the control processor 14, and on computations to be performed by the control processor 14 are also described.

Figure 5:
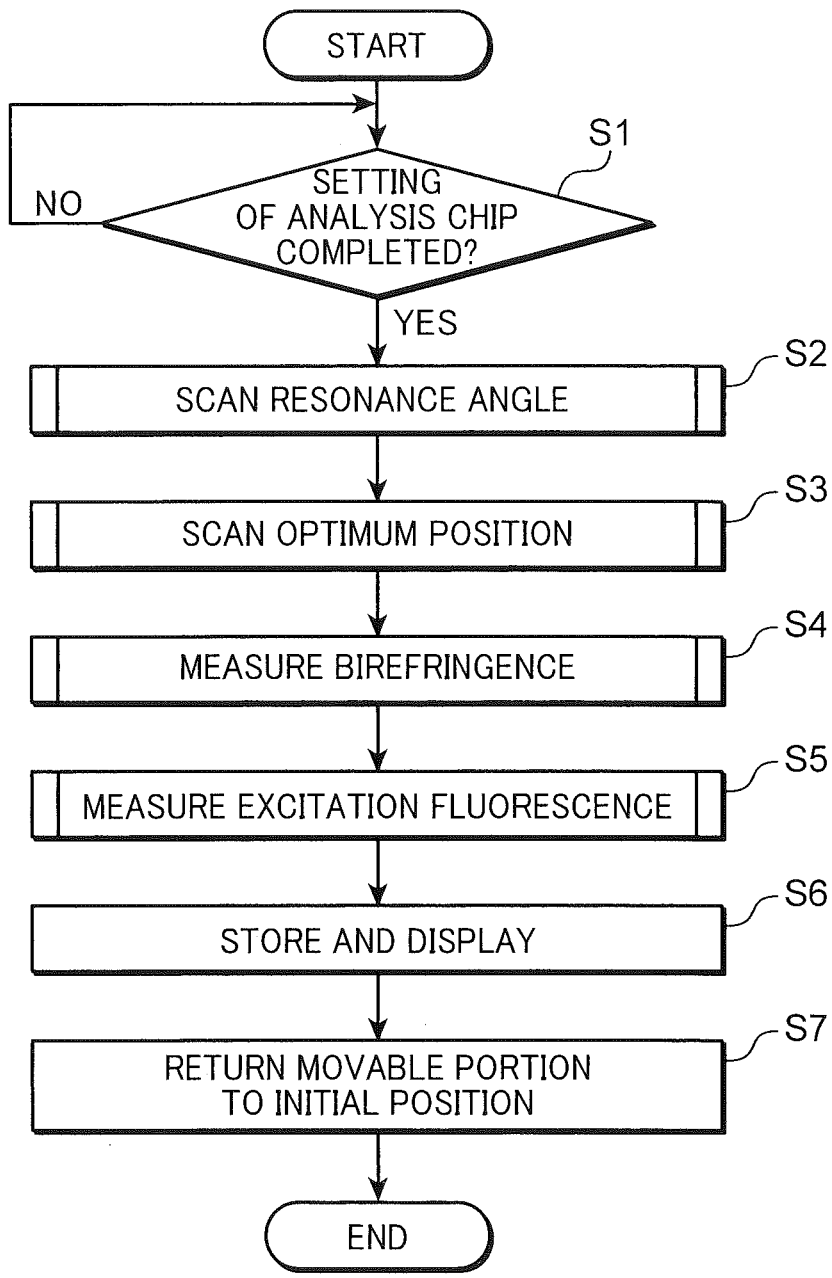
FIG. 5 is a flowchart showing a basic sequence for use in analyzing a specimen by the surface plasmon resonance fluorescence analysis device.
Figure 6:
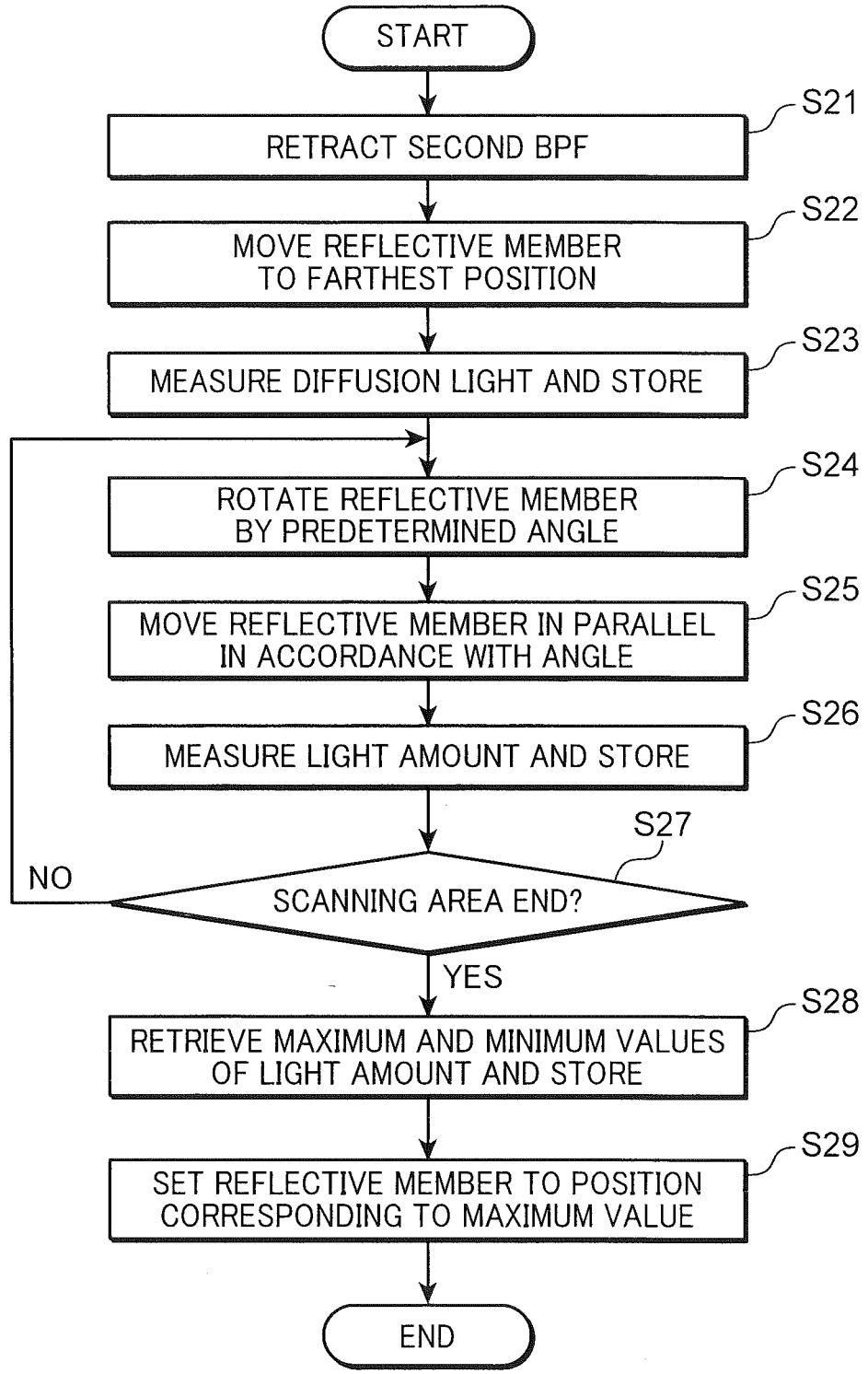
FIG. 6 is a flowchart showing a resonance angle scanning sequence in FIG. 5.
Figure 7:
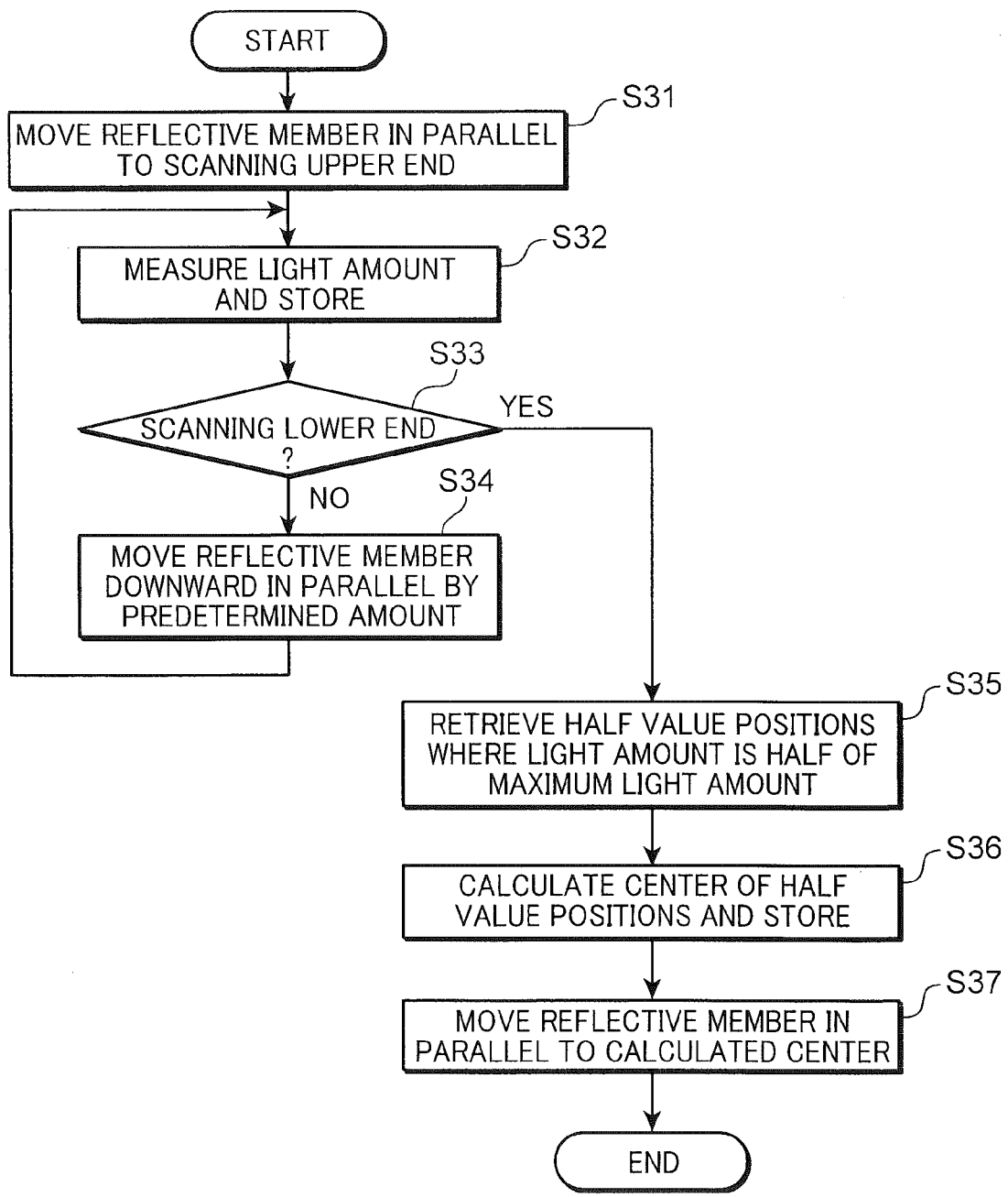
FIG. 7 is a flowchart showing an optimum position scanning sequence in FIG. 5.
Figure 8:
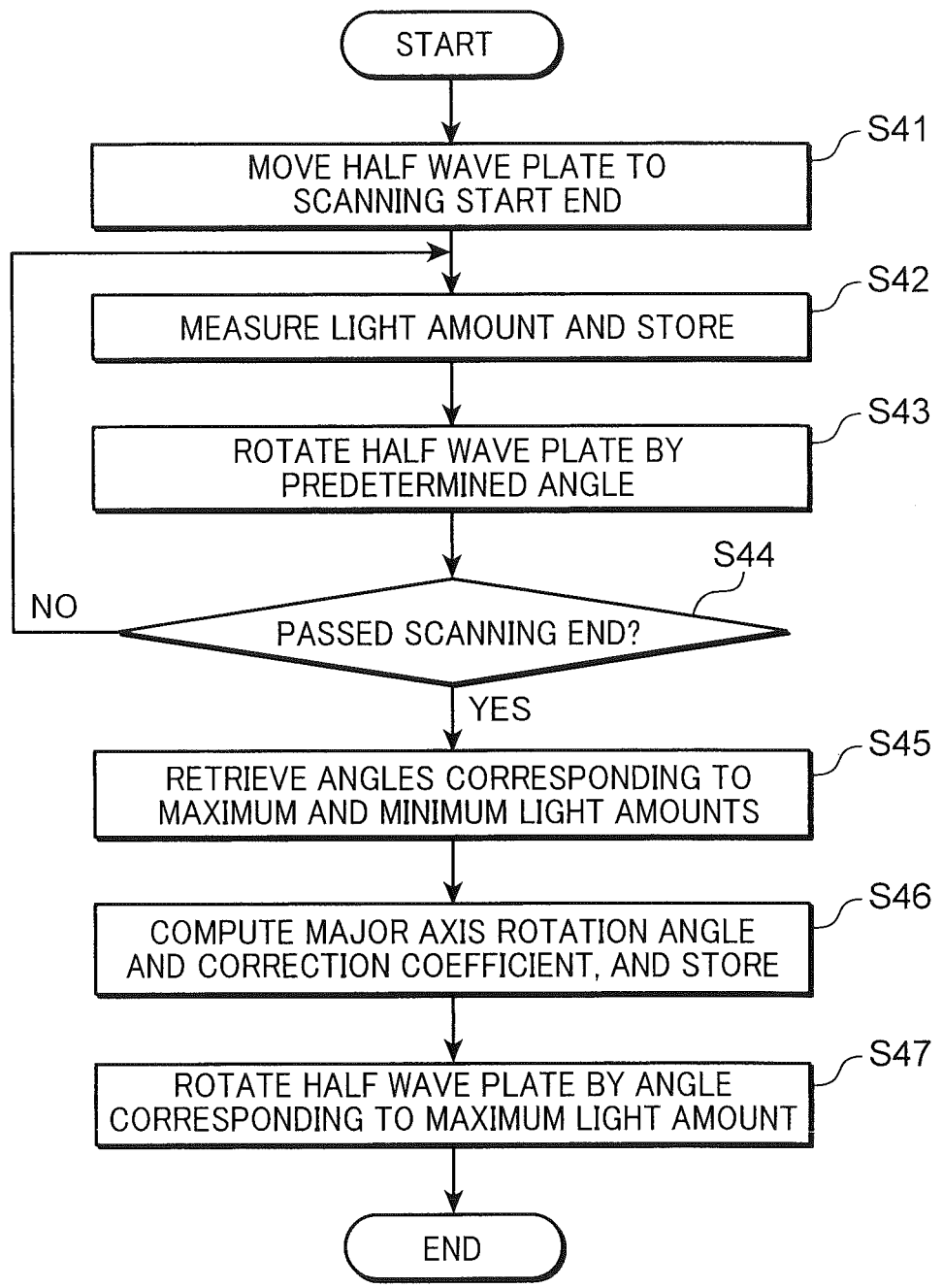
FIG. 8 is a flowchart showing a birefringence measuring sequence in FIG. 5.

FIG. 5 is a flowchart showing a basic sequence to be performed in analyzing a specimen by the analysis device 10. FIG. 6 is a flowchart showing a resonance angle scanning sequence. FIG. 7 is a flowchart showing an optimum position scanning sequence. FIG. 8 is a flowchart showing a birefringence measuring sequence. FIG. 9 is a flowchart showing an excitation fluorescence measuring sequence.

<Pretreatment Process>

For instance, a blood sample is supplied from a patient, and the supplied blood sample is injected to a reagent chip. The reagent chip containing the blood sample is placed in the pretreatment portion of the analysis device 10. The control processor 14 controls the pretreatment portion to perform pretreatment (e.g. blood cell separation, dilution, mixing) of the blood sample contained in the reagent chip placed in the pretreatment portion, whereby a sample solution is prepared. Then, in response to placing the analysis chip 50 in the pretreatment portion, the control processor 14 controls the pretreatment portion to flow the sample solution subjected to the pretreatment into the channel 58 of the analysis chip 50 for capturing a specimen (specific antigen) by the capturing bodies 56 immobilized on the surface of the metal film 55. In other words, the pretreatment portion reacts the capturing bodies 56 with the specimen. In the embodiment, the capturing bodies 56 capture a specimen labeled by a fluorescent material (in the embodiment, a fluorescent pigment). The invention is not limited to the above. For instance, after a specimen is captured by the capturing bodies 56, a fluorescent material may be injected to the analysis chip 50 to thereby label the specimen in a state that the fluorescent material is captured by the capturing bodies 56.

The analysis chip 50 which has undergone the above reaction is transported to the chip holding portion 12, and held on the chip holding portion 12 (Step S1).

<Temperature Adjustment of Excitation Light Source 22>

On the other hand, the excitation light source (in the embodiment, a laser diode) 22 is kept in a constant temperature condition by being constantly subjected to temperature adjustment by the temperature adjusting circuit 25 for outputting output light of a stable wavelength with less wavelength variation. The above operation is essential in a device configured to quantitatively determine e.g. the proteins in a blood sample, because wavelength variation causes a change of the surface plasmon resonance condition or a change of the emerging amount of evanescent wave (enhanced electric field). It takes a certain time to obtain a certain maintenance temperature. Therefore, it is a normal practice that the excitation light source 22 is kept in a certain temperature range by the temperature adjusting circuit 25 from the point of time when the power source of the analysis device 10 is turned on.

<Resonance Angle Scanning Process>

In response to placing the analysis chip 50 on the chip holding portion 12, the control processor 14 performs scanning of an optimum surface plasmon resonance condition (scanning of a resonance angle) with respect to the analysis chip 50. Then, the control processor 14 performs positioning (first positioning) of the reflective member 36, based on the scanning result, so that the excitation light α enters the metal film 55 at the incident angle (excitation incident angle θ1) at which the electric field intensity of an enhanced electric field to be generated on the metal film 55 is maximized (Step S2).

Specifically, the control processor 14 controls the reflective member driving portion 37 to drive the reflective member 36 to thereby scan the incidence condition (excitation incident angle θ1) of the excitation light α with respect to the metal film 55 of the prism 51 included in the analysis chip 50. More specifically, the incident angle θ1 of excitation light at which the intensity of an enhanced electric field (evanescent wave) on the metal film 55 of the prism 51 based on surface plasmon resonance is maximized, is determined by e.g. the material and the shape of the prism 51 to be included in the analysis chip 50, or by the refractive index of a channel filling liquid (sample solution). Nevertheless, the excitation light incidence condition (excitation incident angle θ1) fluctuates by e.g. the molecular weight of a specimen captured by the capturing bodies 56, the components of the molecules of the specimen, or manufacturing error of the prism 51. In view of the above, the control processor 14 causes the excitation light α to enter the metal film 55 at an incident angle in the range of less than ±10° with respect to an excitation incident angle θ1a based on design. Then, an excitation incident angle θ1 with respect to the analysis chip 50 is obtained, based on the light amount of light to be generated on the metal film 55 at the time of light incidence.

More specifically, firstly, the control processor 14 controls the position switching portion 48 of the second wave shaping portion 43 to move the second BPF 46 to the retracted position, and to move the second NDF 47 to the filtering position (Step S21). In performing the above control, the half wave plate 33 of the polarization direction adjusting portion 31 is in an ideal state in terms of design (initial state), in which the P-wave component of the excitation light α to be entered to the metal film 55 that is irradiated with the excitation light α from the excitation light emitting portion 20 is maximized.

The control processor 14 controls the rotation driving mechanism and the reciprocation driving mechanism of the reflective member driving portion 37 to move the reflective member 36 to a farthest position (Step S22). The farthest position is a position of the reflective member 36 and an orientation of the reflective surface 36a, corresponding to an incident angle θ, at which an evanescent wave does not emerge in a region near the surface 55a of the metal film 55 in a state that the excitation light α emitted from the excitation light emitting portion 20 is reflected on a specific position on the metal film 55 (in the embodiment, within the measurement area of the light measuring portion 40).

In the above state, the control processor 14 controls the light measuring portion 40 to measure the light amount of light generated on the metal film 55. Then, the control processor 14 acquires the measurement result of the light measuring portion 40 by an output signal from the light measuring portion 40 (specifically, the light receiving portion 41). The light to be measured by the light measuring portion 40 when the reflective member 36 is in the farthest position is surface diffusion light SK from the prism 51.

The control processor 14 stores the incident angle θ of the excitation light α with respect to the metal film 55, and the light amount of light measured by the light measuring portion 40 in correlation with each other (Step S23). Since the second BPF 46 is in the retracted position when the above operation is performed, the light to be received by the light receiving portion 41 includes light of a same wavelength as the excitation wavelength of the excitation light α. The light of the same wavelength as the excitation wavelength includes plasmon scattering light, Raman scattering light, and diffusion light generated on the metal film 55. These lights of the same wavelength as the excitation wavelength are enhanced by surface plasmon resonance generated on the metal film 55. Therefore, the light amount of light of the same wavelength as the excitation wavelength is sufficiently large, as compared with the light amount of excitation fluorescence generated by excitation of a fluorescent material labeled on a specimen. In view of the above, causing the control processor 14 to control the position switching portion 48 to retract the second BPF 46 from the optical path of the measurement optical system 42 for allowing the light receiving portion 41 to receive the light of the excitation wavelength, is advantageous in precisely measuring the light amount of light to be generated on the metal film 55.

In the embodiment, the light receiving portion 41 for measuring excitation fluorescence of a small light amount is configured to measure e.g. surface plasmon scattering light or diffusion light, whose light amount is significantly larger than the light amount of excitation fluorescence. Accordingly, the analysis device 10 according to the embodiment is configured to cause the position switching portion 48 to retract the second BPF 46 to the retracted position and to move the second NDF 47 to the filtering position, whereby the common light receiving portion (in the embodiment, PMT) 41 is capable of measuring the light amounts of both lights (e.g. scattering light and excitation fluorescence).

The control processor 14 controls the incident path adjusting portion 35 to adjust the position of the reflective member 36 in a state that the excitation light α is emitted from the light source portion 21. Specifically, the control processor 14 controls the rotation driving mechanism to rotate the orientation of the reflective surface 36a (Step S24), and controls the reciprocation driving mechanism to move the position of the reflective member 36 (Step S25), while keeping the irradiation position of the excitation light α from being displaced on the metal film 55. More specifically, the control processor 14 stores in advance in a table in correlation with each other, each respective position of the reflective member 36, and each respective orientation of the reflective surface 36a at which the excitation light α reflected on the reflective surface 36a enters the prism 51 and impinges a specific position on the metal film 55 in a state that the reflective member 36 is positioned at each respective position. Then, the control processor 14 controls the rotation driving mechanism and the reciprocation moving mechanism to move the reflective member 36, based on the table. By performing the above control, even if the position of the reflective member 36 is changed and the orientation of the reflective surface 36a is adjusted by the reciprocation driving mechanism and by the rotation driving mechanism that do not mechanically link to each other, it is possible to change only the incident angle θ with respect to the metal film 55, without changing the irradiation position of the excitation light α on the metal film 55. It should be noted that one of Step S24 and Step S25 may be performed prior to the other of Step S24 and Step S25, and then, the other of Step S24 and Step S25 may be performed; or both of Step S24 and Step S25 may be performed simultaneously.

The light measuring portion 40 measures the light amount of light generated on the metal film 55 and outputs the measurement result by the light measuring portion 40 to the control processor 14, and the control processor 14 stores the measurement result in correlation with the incident angle θ (Step S26).

As described above, the control processor 14 controls the light measuring portion 40 to measure the light amount of light while changing the incident angle θ in such a manner that the irradiation position on the metal film 55 is not displaced, and stores the measurement result by the light measuring portion 40.

The control processor 14 controls the light measuring portion 40 to measure the light amount of light in a predetermined scanning area (e.g. at the incident angle θ in the range of less than ±10° with respect to the excitation incident angle θ1*a* based on design), and thereafter, controls the light source portion 21 to stop the emission of the excitation light α from the light source portion 21 (Step S27). Then, the control processor 14 retrieves a maximum value and a minimum value among the stored light amounts, and stores the retrieved maximum and minimum values (Step S28). Then, the control processor 14 controls the reflective member driving portion 37 to drive the reflective member 36 so that the position of the reflective member 36 and the orientation of the reflective surface 36*a* respectively coincide with the position of the reflective member 36 and with the orientation of the reflective surface 36*a* at which the maximum amount of light was obtained (Step S29).

<Optimum Position Scanning Process>

After the first positioning of the reflective member 36 is completed, the control processor 14 performs positioning (second positioning) of the reflective member 36 so that the irradiation position (incident position) of the excitation light α onto the metal film 55 coincides with a center portion of the measurement area by the light measuring portion 40 (Step S3).

Figure 10A:
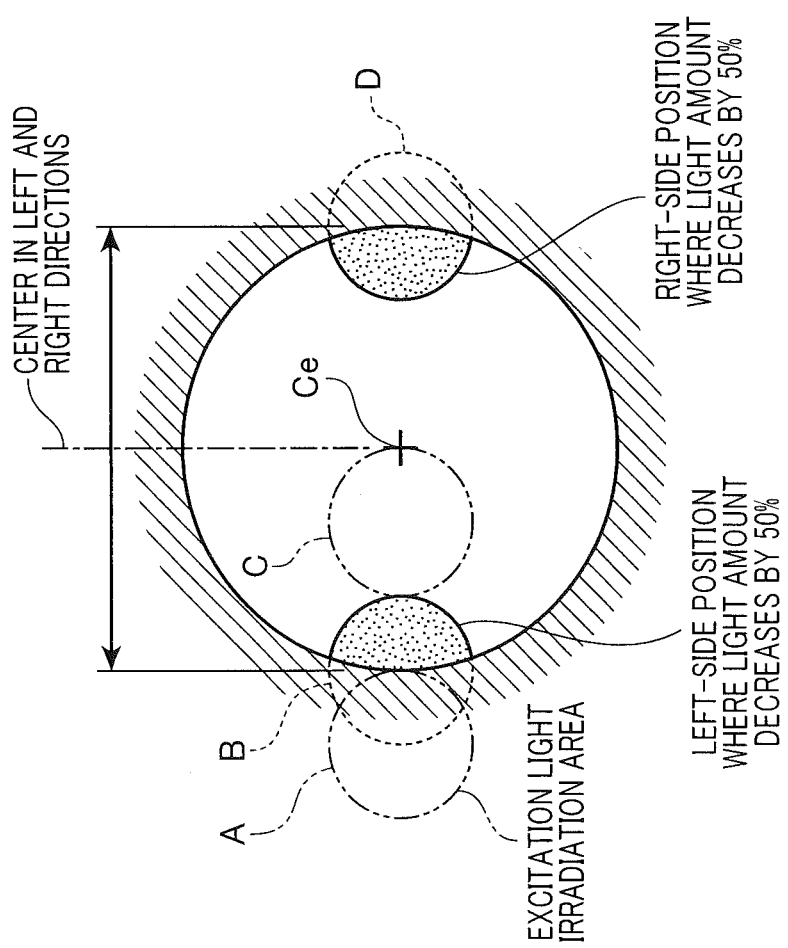
FIG. 10A is a diagram for describing a second positioning of a reflective member in the surface plasmon resonance fluorescence analysis device.

Specifically, firstly, the control processor 14 controls the reciprocation driving mechanism of the reflective member driving portion 37 to move the reflective member 36 to an upper end position (Step S31). The upper end position is a position, where the incident position of the excitation light α on the metal film 55 lies on the outside of the measurement area by the light measuring portion 40 (see the position A in FIG. 10A). The control processor 14 controls the light source portion 21 to emit the excitation light α when the reflective member 36 lies in an area including the above position, controls the light measuring portion 40 to measure the light amount of light generated on the metal film 55 at the time of incidence of the excitation light α, and stores the measurement result by the light measuring portion 40 (Step S32). The control processor 14 determines whether the reflective member 36 is in the lower end position (Step S33). The details on the lower end position will be described later. In the case where it is determined that the reflective member 36 is not in the lower end position, the control processor 14 controls the reciprocation driving mechanism to move the reflective member 36 downward by a predetermined amount (Step S34). When the above control is performed, the control processor 14 controls only the reciprocation driving mechanism to move the reflective member 36, without controlling the rotation driving mechanism to rotate the reflective member 36. In other words, the control processor 14 moves only the position of the reflective member 36, without changing the orientation of the reflective surface 36*a* with respect to the excitation light α from the light source portion 21. After moving the reflective member 36, the control processor 14 controls the light source portion 21 to emit excitation light, controls the light measuring portion 40 to measure the light amount of light generated on the metal film 55 at the time of emitting the excitation light, and stores the measurement result by the light measuring portion 40 (Step S32). Then, the control processor 14 determines whether the reflective member 36 is in the lower end position (Step S33). The control processor 14 repeats Step S32 through Step S34 in this order until the reflective member 36 is moved to the lower end position.

The control processor 14 determines whether the reflective member has reached the lower end position based on a judgment as to whether a light amount i.e. a measurement result by the light measuring portion 40 has decreased by 50% of the maximum amount of light among the stored light amounts. Specifically, the light amount to be measured by the light measuring portion 40 at the beginning of measurement is small, because the irradiation area of the excitation light α on the metal film 55 is on the outside of the measurement area by the light measuring portion 40 at the beginning of the measurement. As the reflective member 36 is gradually moved downward, and the irradiation area of the excitation light α begins to fall in the measurement area by the light measuring portion 40 (see the position B in FIG. 10A), the light amount of light to be measured by the light measuring portion 40 gradually increases. When the reflective member 36 is further moved downward, and the entirety of the irradiation area of the excitation light α completely falls in the measurement area by the light measuring portion 40 (see the position C in FIG. 10A), the light amount of light on the metal film 55 to be measured by the light measuring portion 40 becomes maximum. When the reflective member 36 is furthermore moved downward, the irradiation area of the excitation light α is moved to the outside of the measurement area by the light measuring portion 40, from the side of the measurement area opposite from the incident side of the measurement area (see the position D in FIG. 10A). As a result of the above movement, the light amount of light to be measured by the light measuring portion 40 decreases. In other words, lens vignetting (light falloff at edge portions) occurs. The control processor 14 stores the intensities of the lights, and the up and down positions of the reflective member 36 when the respective intensities are measured in correlation with each other, and determines whether the light amount of the measured light decreases by 50% of the maximum amount of light. Then, the control processor 14 determines that the reflective member 36 has reached the lower end position when the light amount of light to be measured by the light measuring portion 40 has decreased by 50% of the maximum amount of light.

In the case where the control processor 14 determines that the reflective member 36 has moved to the lower end position, the control processor 14 retrieves a value at which the light amount has decreased by 50% of the maximum amount of light, among the values of the stored light amounts (Step S35). There are two values to be retrieved (see the position B and the position D in FIG. 10A). The control processor 14 retrieves each of the positions of the reflective member 36 at which the light amount of light to be measured by the light measuring portion 40 decreased by 50% of the maximum amount of light. Then, the control processor 14 calculates a center position (see the position Ce in FIG. 10A) between the two positions, and stores the calculated center position (Step S36). The control processor 14 controls the reciprocation driving mechanism to move the reflective member 36 for moving the irradiation position to the calculated center position Ce (Step S37: see FIG. 10B).

By performing the above control, it is possible to make the light amount of self fluorescence constant, each time the analysis chip 50 is measured by the light measuring portion 40. Specifically, fluorescence generates in the prism 51 due to the excitation light α travelling through the prism 51 (self fluorescence). Such self fluorescence is weak, as compared with scattering light (such as plasmon scattering light or diffusion light) generated on the metal film 55. However, in the case where the concentration of a specimen in a sample solution is low, self fluorescence may have substantially the same intensity as the excitation fluorescence emitted from a fluorescent material labeled on the specimen. As a result, the self fluorescence may turn out to be noise in measuring excitation fluorescence. Since such self fluorescence is weak, in most of the cases, light near the irradiation area of the excitation light α on the metal film 55 may turn out to be noise in measuring excitation fluorescence. Self fluorescence from the incident side (left side in FIG. 10A) of the measurement area by the light measuring portion 40 becomes an issue, because the excitation light α to be reflected on the metal film 55 is scarce when surface plasmon resonance is generated. The light amount of self fluorescence is proportional to the optical path length. Therefore, it is necessary to adjust the irradiation position of the excitation light α so that the optical path length on the incident side of the measurement area by the light measuring portion 40 is made constant, each time a specimen is analyzed. In view of the above, constantly adjusting the irradiation position of the excitation light α to coincide with the center position on the measurement area by the light measuring portion 40 each time a specimen is analyzed as described above, is advantageous in making the optical path length of the excitation light α constant on the incident side of the measurement area by the light measuring portion 40. As a result of the above adjustment, it is possible to suppress a difference in self fluorescence among the analysis chips 50 (prisms 51). This is advantageous in improving the precision in analyzing specimens.

<Birefringence Measuring Process>

Birefringence occurs when the excitation light α travels through the prism 51. In view of the above, the control processor 14 measures the birefringence (Step S4). Taking into account the birefringence to be measured by the control processor 14 in measuring excitation fluorescence from a fluorescent material labeled on a specimen is advantageous in improving the precision in measuring a specimen. Specifically, birefringence occurs when light is transmitted through a medium. Birefringence increases in the case where light is transmitted through a dielectric body such as a resin member. The birefringence occurs due to e.g. a density difference among media, and the density difference occurs when the media are formed. Therefore, the degree of birefringence differs among individual prisms 51. Phase rotation is generated in the excitation light α travelling through the prism 51 by birefringence, and an S-wave component may be generated in the excitation light α by phase rotation resulting from the birefringence, regardless of an intention to enter only a P-wave component onto the metal film 55. The light amount of excitation fluorescence excited in an enhanced electric field decreases depending on the amount of the S-wave component generated by the birefringence. Accordingly, causing the control processor 14 to correct the light amount by the decreased amount is advantageous in improving detection precision and sensitivity of a specimen by the analysis device 10.

Specifically, the control processor 14 controls the light source portion 21 to emit the excitation light α, and controls the light measuring portion 40 to measure the light amount of light generated on the metal film 55. At the time of the measurement, the half wave plate 33 is set in an initial state (Step S41). Then, the control processor 14 stores the light amount of light measured by the light measuring portion 40 in correlation with the rotation position of the half wave plate 33 (a rotation angle with respect to the initial state), while controlling the rotation driving portion to rotate the half wave plate 33 (Step S42 and Step S43). Rotating the half wave plate 33 by the control processor 14 respectively increases and decreases the P-wave component and the S-wave component of the excitation light α to be entered to the metal film 55. As the P-wave component and the S-wave component increase and decrease, the light amount of light to be measured by the light measuring portion 40 increases and decreases. In performing the above operation, an increase in the P-wave component of the excitation light α results in a decrease in the S-wave component, and a decrease in the P-wave component of the excitation light α results in an increase in the S-wave component. As the P-wave component of the excitation light α to be entered to the metal film 55 increases, the light amount of light to be measured by the light measuring portion 40 increases. On the other hand, as the S-wave component increases, the light amount of light to be measured by the light measuring portion 40 decreases. This is because the P-wave component contributes to surface plasmon resonance, but the S-wave component does not contribute to surface plasmon resonance.

The control processor 14 repeats Step S42 and Step S43 in this order until a maximum value DRmax and a minimum value DRmin of the light amount of light to be measured by the light measuring portion 40 are obtained (Step S44). Then, upon acquiring the maximum value DRmax and the minimum value DRmin, the control processor 14 retrieves the maximum value DRmax and the minimum value DRmin, from the stored light amounts and the stored rotation positions of the half wave plate 33, (Step S45), retrieves the rotation positions of the half wave plate 33 when the respective values are retrieved (specifically, a first rotation position when the maximum value DRmax is obtained, and a second rotation position when the minimum value DRmin is obtained), and stores the retrieved values and the retrieved rotation positions.

Then, the control processor 14 derives a major axis rotation amount θi by birefringence in the prism 51, and a correction coefficient K, based on the formula (1) and the formula (2), using the stored maximum value DRmax, the stored minimum value DRmin, and the light amount of surface diffusion light SK that is stored in the resonance angle scanning process, and stores the derived major axis rotation amount θi and the derived correction coefficient K (Step S46).

$$\theta_i = \arctan\sqrt{\frac{DR_{min} - SK}{DR_{max} - SK}} \quad (1)$$

$$K = \frac{1}{\cos^2\theta} \quad (2)$$

Then, the control processor 14 controls the rotation driving portion 34 to rotate the half wave plate 33 to the rotation position at which the maximum value DRmax was obtained. By performing the above control, the excitation light α is caused to enter the metal film 55 in a state that the P-wave component is largest (in other words, in a state that the S-wave component is smallest).

<Excitation Fluorescence Measuring Process>

Next, the control processor 14 controls the light source portion 21 to irradiate the excitation light α onto the reflective member 36 which has undergone the first positioning and the second positioning. By performing the above control, the excitation light α causes surface plasmon resonance on the metal film 55. Then, the fluorescent material labeled on the specimen and captured by the capturing bodies 56 on the metal film 55 is excited by the enhanced electric field based on the surface plasmon resonance, whereby fluorescence (excitation fluorescence) is emitted. Then, the control processor 14 controls the light measuring portion 40 to measure the excitation fluorescence (Step S5).

Specifically, the control processor 14 controls the position switching portion 48 to move the second BPF 46 to the filtering position, and to retract the second NDF 47 to the retracted position (Step S51: see FIG. 1 and FIG. 4). Then, the control processor 14 controls the rotation driving mechanism of the reflective member driving portion 37 to rotate the reflective member 36 to such a position that the excitation light α emitted from the light source portion 21 enters the non-reflective light absorbing material on the back surface 36b of the reflective member 36 (Step S52). By performing the above control, the prism 51 is brought to a state that the excitation light α is not incident. When the prism 51 is brought to the above state, the control processor 14 controls the light measuring portion 40 to perform a measurement, and stores an output (dark noise DN) from the light measuring portion 40 (Step S53). Then, the control processor 14 controls the rotation driving mechanism of the reflective member driving portion 37 to rotate the reflective member 36 to such a position that the excitation light α from the light source portion 21 enters the reflective surface 36a of the reflective member 36 (Step S54). The orientation of the reflective surface 36a in the above state is the orientation defined in Step S29 of the resonance angle scanning process.

The control processor 14 controls the light source portion 21 to emit the excitation light α, controls the light measuring portion 40 to measure the light amount of excitation fluorescence resulting from an enhanced field generated near the metal film 55, and stores the measurement result by the light measuring portion 40 (Step S55). By performing the above control, the control processor 14 obtains a measurement maximum amount of light (first light amount value) Smax. The measurement maximum amount of light is obtained because the half wave plate 33 is rotated to the first rotation position obtained in the birefringence measuring process (in other words, the rotation position at which the light amount of light to be generated on the metal film 55 irradiated with the excitation light α is equal to the maximum value DRmax), and the intensity of the enhanced electric field near the metal film 55 is largest.

Then, the control processor 14 controls the rotation driving portion 34 to rotate the half wave plate 33 to the second rotation position obtained in the birefringence process (i.e. the rotation position at which the light amount of light to be generated on the metal film 55 irradiated with the excitation light α is equal to the minimum value DRmin) (Step S56). Then, the control processor 14 controls the light measuring portion 40 to measure the light amount of the excitation fluorescence, and stores the measurement result by the light measuring portion 40 (Step S57). By performing the above control, the control processor 14 obtains a measurement minimum light amount (second light amount value) 5 min.

Then, the control processor 14 derives a light amount h of the self fluorescence by the prism and a light amount H of the excitation fluorescence, as expressed by the following formulas (3-1) through (8), using the stored measurement maximum amount of light Smax, the stored measurement minimum light amount 5 min, and the stored dark noise DN; and stores the derived values (Step S58). Here, let it be assumed that $H_1$ is the light amount of excitation fluorescence and h1 is the light amount of self fluorescence when Smax was obtained; and H2 is the light amount of excitation fluorescence and h2 is the light amount of self fluorescence when Smin was obtained.

Firstly, the formula (4) is derived from the formulas (3-1), (3-2) and (3-3).

$$S_{max} = H_1 + h_1 + DN \tag{3-1}$$

$$S_{min} = H_2 + h_2 + DN \tag{3-2}$$

$$H_2 = H_1 \times \tan^2\theta \tag{3-3}$$

Then, $$h_2 - h_1 \times \tan^2\theta = (S_{min} - DN) - (S_{max} - DN) \times \tan^2\theta = A \tag{4}$$

Further, the formula (6) is derived from the formula (5).

$$h_1 : h_2 = 1 + \sin^2\theta : 1 + \cos^2\theta \tag{5}$$

Then, $$h_2 = h_1 \times \frac{1 + \cos^2\theta}{1 + \sin^2\theta} = h_1 \times B \tag{6}$$

Then, the formulas (7-1) and (7-2) are derived from the formula (4) and from the formula (6).

$$h_1 = \frac{A}{B - \tan^2\theta} \tag{7-1}$$

$$H_1 = S_{max} - DN - \frac{A}{B - \tan^2\theta} \tag{7-2}$$

Then, the formula (8) is derived using the correction coefficient K obtained in the birefringence measuring process.

$$H = H_1 \times K \tag{8}$$

In the case where the prism 51 is made of a material with no birefringence, or a material (including resin) having a very small birefringence, the control processor 14 obtains the light amount H of excitation fluorescence, using the following approximation formula (9).

$$H = S_{max} - \frac{S_{min}}{2} - \frac{DN}{2} \tag{9}$$

Further, in the case of using a measurement system in which the amount of dark noise (DN) is very small, the control processor 14 obtains the light amount H of excitation fluorescence, using the following approximation formula (10).

$$H = S_{max} - \frac{S_{min}}{2} \tag{10}$$

<Storage/Display Process>

As described above, after obtaining a true light amount H of excitation fluorescence free from an influence of birefringence and the like, the control processor 14 stores the true light amount H in association with the specimen number (Step S6). Then, the control processor 14 erases the data other than the above. Further, the control processor 14 outputs, to the display portion 16, information based on the light amount H of excitation fluorescence that is stored in association with the specimen number. The display portion 16 displays the information based on the light amount H.

Lastly, the control processor 14 returns the reflective member 36 to the initial position (Step S7), and the sequence of measurements is finished.

According to the embodiment, the incident angle θ of the excitation light α with respect to the metal film 55 can be changed by driving the reflective member 36. Accordingly, it is possible to suppress displacement of the reflection position of the excitation light α on the metal film 55 resulting from a change in the incident angle θ. In other words, in the above configuration, the incident angle θ of the excitation light α with respect to the metal film 55 is changed by changing and adjusting the position of the reflective member 36 and the orientation of the reflective surface 36a. Accordingly, unlike a conventional configuration, in which the incident angle θ is adjusted by moving the entirety of an excitation optical system constituted of a light source and lenses, the above configuration is advantageous in suppressing the number of movable components and the weight of a movable portion. Thus, it is possible to suppress driving error or fluctuation of the movable portion. Consequently, it is possible to optimally suppress displacement of the reflection position of the excitation light α on the metal film 55 resulting from a change in the incident angle θ of the excitation light α.

Further, the analysis device 10 is operable to generate an enhanced electric field based on surface plasmon resonance in the vicinity of the metal film 55 by causing one excitation light α to enter the prism 51. This is advantageous in preventing an increase in the light amount of self fluorescence, which may occur in a conventional configuration, in which multiple excitation lights α, α, . . . having different incident angles θ are caused to simultaneously enter the prism 51. The above configuration is advantageous in suppressing lowering of the S/N ratio of a signal to be obtained by measuring light generated near the metal film 55 by surface plasmon resonance due to self fluorescence.

Further, according to the embodiment, the incident angle θ of the excitation light α with respect to the metal film 55 is precisely set in such a manner that the electric field intensity of an enhanced electric field by surface plasmon resonance is maximized. Specifically, although the absorption peak of reflection light on the metal film 55 in angle spectroscopy, and the peak of the electric field intensity of the enhanced electric field are displaced from each other, the peak of intensity of light (light to be generated on the metal film 55) to be generated resulting from surface plasmon resonance coincides with the peak of the electric field intensity of the enhanced electric field. Accordingly, adjusting the reflective member 36 in such a manner that the position of the reflective member 36 and the orientation of the reflective surface 36a respectively coincide with the position of the reflective member 36 and with the orientation of the reflective surface 36a at which the light amount of light to be generated on the metal film 55 is maximized, enables to set the incident angle of the excitation light α with respect to the metal film 55 to be equal to the excitation incident angle θ1 at which the electric field intensity of the enhanced electric field is maximized.

Further, according to the embodiment, the influence of self fluorescence from the prism 51 is removed from a measurement result to thereby secure a wide dynamic range.

Specifically, by measuring light to be generated on the metal film 55 while changing the polarization direction of the excitation light α with respect to the metal film 55, it is possible to respectively obtain a rotation position of the half wave plate 33 at which the S-wave component (a component that contributes to surface plasmon resonance) of excitation light reflected on the metal film 55 is maximized, and a rotation position of the half wave plate 33 at which the P-wave component (a component that contributes to surface plasmon resonance) of the excitation light is maximized, resulting from an increase or a decrease in the light amount (intensity) of detected light. Then, the half wave plate 33 is adjusted so that the polarization direction of the excitation light coincides with the rotation position of the half wave plate 33, at which the S-wave component is maximized at the time of reflection on the metal film 55. Then, by measuring the excitation fluorescence in the above state by the light measuring portion 40, the light amount of self fluorescence from the prism 51 is obtained. By performing the above control, it is possible to remove the influence of self fluorescence, from a measurement result of excitation fluorescence by the light measuring portion 40, in the case where the half wave plate 33 is adjusted and the P-wave component is maximized at the time of incidence of polarized excitation light α onto the metal film 55. This enables to extract excitation fluorescence. Thus, the analysis device 10 is operable to precisely detect excitation fluorescence, while suppressing an influence of self fluorescence. This is advantageous in securing a wide dynamic range.

Further, according to the embodiment, it is possible to detect a specimen with high sensitivity and with high precision. Specifically, by measuring a light amount of light to be generated on the metal film 55 by surface plasmon resonance, it is possible to precisely obtain the incident angle (excitation incident angle) θ1 of the excitation light α with respect to the film 55, at which the intensity of an enhanced electric field to be formed near the surface 55a of the metal film 55 is maximized. At the time of incidence of the excitation light α, light to be generated on the metal film 55 is light of an excitation wavelength such as plasmon scattering light or surface diffusion light. Accordingly, by switching the position of the second BPF 46 for cutting off the above wavelength component to the retracted position, it is possible to precisely measure an increase or a decrease in the light amount of light to be generated on the metal film 55 based on surface plasmon resonance. Further, at the time of detecting a specimen, the second BPF 46 is inserted on the optical path of the measurement optical system 42, whereby the light component of the excitation wavelength such as plasmon scattering light or surface diffusion light is removed from the light to be measured by the light measuring portion 40. By performing the above control, it is possible to precisely measure excitation fluorescence emitted from a fluorescent material labeled on a specimen. This is advantageous in detecting a specimen with high precision and with high sensitivity, while securing a high S/N ratio of a signal to be obtained by measurement.

It is needless to say that the surface plasmon resonance fluorescence analysis device and the surface plasmon resonance fluorescence analysis method of the invention are not limited to the embodiment, but various modifications and/or alterations are applicable as far as such modifications and/or alterations do not depart from the gist of the invention.

In the analysis device 10 according to the embodiment, analysis chips 50 are replaced one after another, each time a specimen is detected. The invention is not limited to the above. Specifically, the analysis device 10 may be configured in such a manner that an analysis chip is incorporated in a part of the analysis device 10 and detections of specimens are performed by repeatedly using the one analysis chip.

In the resonance angle scanning process of the embodiment, the control processor 14 measures an intensity (in the embodiment, a light amount) of light to be generated on the metal film 55 while continuously changing the incident angle θ of the excitation light α with respect to the metal film 55 in obtaining the excitation incident angle θ1. The invention is not limited to the above.

For instance, the control processor 14 may perform a first scanning operation of measuring a light amount of light to be generated on the metal film 55 at each respective incident angle θ while intermittently changing the incident angle θ (e.g. at an interval of 1° of the incident angle) in a first range, and may perform a second scanning operation of measuring a light amount of light to be generated on the metal film 55 while intermittently or continuously changing the incident angle θ so that the interval of the incident angle θ is set smaller than that in the first scanning operation (e.g. at an interval of 0.1° of the incident angle) in a second range based on the result of the first scanning operation. In other words, the control processor 14 may define the second range based on the first scanning operation, using a discrete step, and thereafter, may obtain the excitation incident angle θ1, at which the light amount of light to be generated on the metal film 55 is equal to the maximum amount of light by finely scanning in the thus defined second range. It should be noted that the second range is included in the first range.

Specifically, the control processor 14 changes the incident angle θ at an interval of 1° in a range (first range) of the incident angle θ of less than ±10° with respect to the excitation incident angle θ1a based on design. At the time of changing the incident angle θ, the control processor 14 measures a light amount of light to be generated on the metal film 55 at each respective incident angle θ (first scanning operation), and stores the measurement result in association with a corresponding incident angle θ. Then, the control processor 14 changes the incident angle θ at an interval of 0.1° in a range (second range) of the incident angle θ of ±1° or less with respect to the incident angle θ, at which the maximum amount of light was obtained by the first scanning operation, or continuously changes the incident angle θ. At the time of performing the above control, the control processor 14 measures a light amount of light to be generated on the metal film 55 (second scanning operation), and stores the measurement result in association with a corresponding incident angle θ. Then, the control processor 14 defines the incident angle θ at which the maximum amount of light was obtained, as the excitation incident angle θ1 in the second scanning operation. The above configuration is advantageous in efficiently determining the excitation incident angle θ1 at which the enhanced electric field is maximized, as compared with a configuration in which the overall of the first range is finely scanned.

In the case where the first scanning operation and the second scanning operation are performed in the resonance angle scanning process, and the analysis device 10 sequentially analyzes specimens, while holding analysis chips 50 one after another on the chip holding portion 12, the first scanning operation may be performed only for a first analysis chip 50, and only the second scanning operation may be performed for a second analysis chip 50 and thereafter.

Specifically, for instance, the control processor 14 changes, with respect to the first analysis chip 50, the incident angle θ at an interval of 1° in a range (first range) of the incident angle θ of less than ±10° with respect to the excitation incident angle θ1a based on design. In performing the above control, the control processor 14 measures a light amount of light to be generated on the metal film 55 at each respective incident angle θ (first scanning operation), and stores the measurement result in association with a corresponding incident angle θ. Then, the control processor 14 changes the incident angle θ at an interval of 0.1° in a range (second range) of the incident angle θ of ±3° or less with respect to the incident angle θ, at which the maximum amount of light was obtained in the first scanning operation, or continuously changes the incident angle θ. In performing the above control, the control processor 14 measures a light amount of light to be generated on the metal film 55 (second scanning operation), and stores the measurement result in association with a corresponding incident angle θ. Then, the control processor 14 defines the incident angle θ at which the maximum amount of light was obtained in the second scanning operation, as the excitation incident angle θ1 with respect to the first analysis chip 50.

Then, the control processor 14 changes, with respect to the second analysis chip 50, the incident angle θ at an interval of 0.1° in the second scanning range obtained by the first scanning operation with respect to the first analysis chip 50, or continuously changes the incident angle θ, without performing the first scanning operation. In performing the above control, the control processor 14 measures a light amount of light to be generated on the metal film 55 (second scanning operation), and stores the measurement result in association with a corresponding incident angle θ. Then, the control processor 14 defines the incident angle θ at which the maximum amount of light was obtained in the second scanning operation, as the excitation incident angle θ1 with respect to the second analysis chip 50. As described above, regarding the second analysis chip 50 and thereafter, the control processor 14 performs only the scanning operation (second scanning operation) in the second range which was obtained with respect to the first analysis chip 50. This is advantageous in shortening the analysis time.

Summary of the Embodiment

The following is a summary of the embodiment.

The surface plasmon resonance fluorescence analysis device according to the embodiment is a surface plasmon resonance fluorescence analysis device for measuring fluorescence emitted by excitation of a fluorescent material labeled on a specimen by an electric field based on surface plasmon resonance. The surface plasmon resonance fluorescence analysis device includes a chip holding portion which is configured to detachably hold an analysis chip including a prism having a metal film formed on a predetermined surface thereof; a light source portion which emits excitation light for causing surface plasmon resonance on the metal film; and an incident path adjusting portion which allows the excitation light to enter the prism of the analysis chip held on the chip holding portion by reflection of the excitation light emitted from the light source portion. The incident path adjusting portion includes a reflective member having a reflective surface formed thereon for reflecting the excitation light from the light source portion, and a driving portion for driving the reflective member. The driving portion is configured to change a position of the reflective member and to adjust an orientation of the reflective surface in such a manner that the excitation light entered the prism is reflected at a specific position on the metal film.

Further, a surface plasmon resonance fluorescence analysis device according to another aspect is a surface plasmon resonance fluorescence analysis device for measuring fluorescence emitted by excitation of a fluorescent material labeled on a specimen by an electric field based on surface plasmon resonance. The surface plasmon resonance fluorescence analysis device includes a prism having a metal film formed on a predetermined surface thereof; a light source portion which emits excitation light for causing surface plasmon resonance on the metal film; and an incident path adjusting portion which allows the excitation light to enter the prism by reflection of the excitation light emitted from the light source portion. The incident path adjusting portion may include a reflective member having a reflective surface formed thereon for reflecting the excitation light from the light source portion, and a driving portion for driving the reflective member. The driving portion may be configured to change a position of the reflective member and to adjust an orientation of the reflective surface in such a manner that the excitation light entered the prism is reflected at a specific position on the metal film.

In the above configurations, it is possible to change the incident angle of the excitation light with respect to the metal film by driving the reflective member. This is advantageous in suppressing displacement of the reflection position of the excitation light on the metal film, resulting from a change in the incident angle. In other words, according to the above configurations, changing the position of the reflective member and adjusting the orientation of the reflective surface change the incident angle of the excitation light with respect to the metal film. This is advantageous in suppressing the number of movable components and the weight of a movable portion, as compared with a conventional configuration, in which the incident angle is adjusted by moving the entirety of an excitation optical system constituted of a light source and lenses. Accordingly, it is possible to suppress driving error or fluctuation of the movable portion. Consequently, it is possible to optimally suppress displacement of the reflection position of the excitation light on the metal film resulting from a change in the incident angle of the excitation light.

Further, the analysis device is configured to generate an enhanced electric field based on surface plasmon resonance in the vicinity of the metal film by causing one excitation light to enter the prism. This is advantageous in preventing an increase in the light amount of self fluorescence, which may occur in a conventional configuration, in which multiple excitation lights having different incident angles are caused to simultaneously enter the prism. The above configuration is advantageous in suppressing lowering of the S/N ratio of a signal to be obtained by measuring light generated near the metal film by surface plasmon resonance due to self fluorescence.

Preferably, the surface plasmon resonance fluorescence analysis device may further include a light measuring portion which is configured to measure an intensity of light to be generated on a side of the metal film opposite from a side of the prism by reflection of the excitation light on the metal film; and a control portion which controls the driving portion and the light measuring portion. The control portion controls the driving portion to perform first positioning of the reflective member, the first positioning being such that the control portion controls the light measuring portion to measure the intensity of light to be generated on the opposite side of the metal film while changing an incident angle of the excitation light with respect to the metal film by controlling the driving portion to change the position of the reflective member and to adjust the orientation of the reflective surface, and thereafter, the control portion controls the driving portion so that the position of the reflective member and the orientation of the reflective surface respectively coincide with a position of the reflective member and with an orientation of the reflective surface when a maximum amount of light is detected by the light measuring portion.

In the above configuration, the incident angle of the excitation light with respect to the metal film is precisely set in such a manner that the electric field intensity of the enhanced electric field by surface plasmon resonance is maximized. Specifically, although the absorption peak of reflection light on the metal film in angle spectroscopy, and the peak of the electric field intensity of the enhanced electric field are displaced from each other, the peak of intensity of light (light to be generated on the side of the metal film opposite from the side of the prism) generated resulting from surface plasmon resonance coincides with the peak of the electric field intensity of the enhanced electric field. Accordingly, adjusting the reflective member in such a manner that the position of the reflective member and the orientation of the reflective surface respectively coincide with the position of the reflective member and with the orientation of the reflective surface at which the intensity of light to be generated on the side of the metal film opposite from the side of the prism is maximized, enables to make the incident angle of the excitation light with respect to the metal film equal to the angle at which the electric field intensity of the enhanced electric field is maximized.

Preferably, the control portion may perform a first scanning operation of measuring an intensity of light to be generated on the opposite side of the metal film at each respective incident angle while intermittently changing the incident angle in a first range, the first range being a range of the incident angles of the excitation light with respect to the metal film; and may perform a second scanning operation of measuring an intensity of light to be generated on the opposite side of the metal film intermittently at an interval smaller than an interval of the incident angle in the first scanning operation, or may perform a second scanning operation of measuring an intensity of light to be generated on the opposite side of the metal film while continuously changing the incident angle, in a second range to be defined based on a result of the first scanning operation, for obtaining the maximum amount of light. Preferably, the second range may be included in the first range.

In the above configuration, the range of the incident angles within which the second scanning operation is performed is defined, based on the measurement result of the intensity (light amount) of light to be generated on the opposite side of the metal film at each respective incident angle, which is obtained by measurement while intermittently changing the incident angle of the excitation light. Then, it is possible to efficiently determine the incident angle that maximizes the enhanced electric field by finely scanning the thus defined range, as compared with a configuration in which the overall of the first range is finely scanned.

Preferably, in the above configuration, the control portion may be configured to store the second range with respect to a specific prism, and to obtain the maximum amount of light by performing the second scanning operation based on the stored second range, without performing the first scanning operation with respect to a prism other than the specific prism.

In the case where plural prisms (or analysis chips) are replaced one after another for detection of specimens, the second range is defined by analysis of a specimen by a specific prism, and the first scanning operation is omitted in analysis of a specimen by another prism (or another analysis chip). Thus, the configuration is advantageous in shortening the analysis time.

Preferably, the driving portion may be configured to move the reflective member in a direction orthogonal to a reflection plane of the metal film where the excitation light is reflected, while maintaining the orientation of the reflective surface with respect to the metal film, and the control portion may perform, after performing the first positioning, second positioning of the reflective member in the direction orthogonal to the reflection plane based on a measurement result obtained by controlling the driving portion to move the reflective member in the direction orthogonal to the reflection plane, and by controlling the light measuring portion to measure an intensity of light to be generated on the opposite side of the metal film.

In the above configuration, even if prisms (or analysis chips) are replaced one after another, the light amount of self fluorescence is made constant in a measurement area for measuring light resulting from an enhanced electric field, each time the prism is replaced. This enables to further enhance the analysis precision of a specimen. Specifically, after the first positioning is performed, the intensity of light to be generated on the opposite side of the metal film is measured, while moving the reflective member in the direction orthogonal to the reflection plane in a state that the orientation of the reflective surface with respect to the metal film is maintained. At the measurement, it is possible to detect that the reflection position has moved to an end of the measurement area, utilizing a feature that the light amount to be measured lowers in the case where the reflection position of the excitation light is deviated from the measurement area. In this way, it is possible to detect the position of the reflective member in the case where the reflection position is moved to one of both ends of the measurement area, and the reflective member is moved in the orthogonal direction based on the detection result. This enables to make the reflection position of the excitation light in the measurement area constant. Thus, the optical path length of the excitation light travelling through the prism is made constant in the measurement area. Consequently, it is possible to make the light amount of self fluorescence resulting from the excitation light constant, even if prisms and the like are replaced.

Preferably, the control portion may be configured to store, in a table in correlation with each other, a position of the reflective member, and an orientation of the reflective surface at which the excitation light reflected on the reflective surface enters the prism and impinges the specific position on the metal film when the reflective member is positioned at the position, and to perform the first positioning of the reflective member based on the table.

In the above configuration, even if the driving portion changes the position of the reflective member and adjusts the orientation of the reflective surface individually, it is possible to change only the incident angle with respect to the metal film, without changing the reflection position of the excitation light on the metal film.

Preferably, the reflective member may be a dielectric multilayer mirror.

In the above configuration, phase displacement or dimming of light does not occur in excitation light before incidence onto the reflective surface, and in excitation light after reflection on the reflective surface. This is advantageous in precisely detecting a specimen.

Further, the surface plasmon resonance fluorescence analysis method according to the embodiment is a surface plasmon resonance fluorescence analysis method for measuring light emitted by excitation of a fluorescent material labeled on a specimen by an electric field based on surface plasmon resonance. The surface plasmon resonance fluorescence analysis method includes a preparation step of preparing a prism having a metal film formed on a predetermined surface thereof, and of allowing a sample solution containing the specimen to flow on the metal film; an excitation light emission step of emitting excitation light for causing surface plasmon resonance on the metal film; a resonance angle scanning step of changing an incident angle of the excitation light with respect to the metal film while maintaining a state in which the excitation light that is reflected on a reflective surface of the reflective member and enters the prism is reflected at a specific position on the metal film, by changing a position of the reflective member having the reflective surface formed thereon for reflecting the excitation light, and by adjusting an orientation of the reflective surface, and of measuring an intensity of light to be generated on a side of the metal film opposite from a side of the prism by reflection of the excitation light on the metal film; and a positioning step of performing positioning of the reflective member in such a manner that the position of the reflective member and the orientation of the reflective surface respectively coincide with a position of the reflective member and with an orientation of the reflective surface when a maximum amount of light is measured in the scanning step.

In the above configuration, the incident angle of the excitation light with respect to the metal film is adjusted by adjusting the position of the reflective member and the orientation of the reflective surface. This is advantageous in suppressing displacement of the reflection position of the excitation light on the metal film resulting from a change in the incident angle, as compared with a configuration, in which the incident angle is adjusted by moving the entirety of an excitation optical system. Further, an enhanced electric field is generated by causing one excitation light to enter the prism. This is advantageous in suppressing lowering of the S/N ratio of a signal to be obtained by measuring light generated near the metal film by surface plasmon resonance due to self fluorescence, unlike a conventional configuration, in which multiple excitation lights having different incident angles are caused to simultaneously enter the prism.

Further, the above configuration is advantageous in precisely setting the incident angle of the excitation light with respect to the metal film in such a manner that the electric field intensity of an enhanced electric field by surface plasmon resonance is maximized.

INDUSTRIAL APPLICABILITY

As described above, the surface plasmon resonance fluorescence analysis device and the surface plasmon resonance fluorescence analysis method of the invention are useful in causing a fluorescent material contained in a specimen to emit fluorescence, utilizing an electric field of an evanescent wave generated by surface plasmon resonance, and in measuring the specimen by detecting the fluorescence. Thus, the surface plasmon resonance fluorescence analysis device and the surface plasmon resonance fluorescence analysis method of the invention are suitable for suppressing displacement of the reflection position of excitation light on a metal film, while suppressing lowering of the S/N ratio of a signal to be obtained by measuring light resulting from an enhanced electric field that is generated near the metal film on a prism.

The invention claimed is:

1. A surface plasmon resonance fluorescence analysis device for measuring fluorescence emitted by excitation of a fluorescent material labeled on a specimen by an electric field based on surface plasmon resonance, the surface plasmon resonance fluorescence analysis device comprising:
   a chip holding portion which is configured to detachably hold an analysis chip including a prism having a metal film formed on a predetermined surface thereof;
   a light source portion which emits excitation light for causing surface plasmon resonance on the metal film; and
   an incident path adjusting portion which allows the excitation light to enter the prism of the analysis chip held on the chip holding portion by reflection of the excitation light emitted from the light source portion, wherein
   the incident path adjusting portion includes a reflective member having a reflective surface formed thereon for reflecting the excitation light from the light source portion, and a driving portion for driving the reflective member, and
   the driving portion is configured to change a position of the reflective member and to adjust an orientation of the reflective surface in such a manner that the excitation light entered the prism is reflected at a specific position on the metal film.

2. The surface plasmon resonance fluorescence analysis device according to claim 1, further comprising:
a light measuring portion which is configured to measure an intensity of light to be generated on a side of the metal film opposite from a side of the prism by reflection of the excitation light on the metal film; and
a control portion which controls the driving portion and the light measuring portion, wherein
the control portion controls the driving portion to perform first positioning of the reflective member, the first positioning being such that the control portion controls the light measuring portion to measure the intensity of light to be generated on the opposite side of the metal film while changing an incident angle of the excitation light with respect to the metal film by controlling the driving portion to change the position of the reflective member and to adjust the orientation of the reflective surface, and thereafter, the control portion controls the driving portion so that the position of the reflective member and the orientation of the reflective surface respectively coincide with a position of the reflective member and with an orientation of the reflective surface when a maximum amount of light is detected by the light measuring portion.

3. The surface plasmon resonance fluorescence analysis device according to claim 2, wherein
the control portion performs a first scanning operation of measuring an intensity of light to be generated on the opposite side of the metal film at each respective incident angle while intermittently changing the incident angle in a first range, the first range being a range of the incident angles of the excitation light with respect to the metal film; and performs a second scanning operation of measuring an intensity of light to be generated on the opposite side of the metal film intermittently at an interval smaller than an interval of the incident angle in the first scanning operation, or performs a second scanning operation of measuring an intensity of light to be generated on the opposite side of the metal film while continuously changing the incident angle, in a second range to be defined based on a result of the first scanning operation, for obtaining the maximum amount of light, and
the second range is included in the first range.

4. The surface plasmon resonance fluorescence analysis device according to claim 3, wherein
the control portion is configured to store the second range with respect to a specific prism, and to obtain the maximum amount of light by performing the second scanning operation based on the stored second range, without performing the first scanning operation with respect to a prism other than the specific prism.

5. The surface plasmon resonance fluorescence analysis device according to claim 2, wherein
the driving portion is configured to move the reflective member in a direction orthogonal to a reflection plane of the metal film where the excitation light is reflected, while maintaining the orientation of the reflective surface with respect to the metal film, and
the control portion performs, after performing the first positioning, second positioning of the reflective member in the direction orthogonal to the reflection plane based on a measurement result obtained by controlling the driving portion to move the reflective member in the direction orthogonal to the reflection plane, and by controlling the light measuring portion to measure an intensity of light to be generated on the opposite side of the metal film.

6. The surface plasmon resonance fluorescence analysis device according to claim 2, wherein
the control portion is configured to store, in a table in correlation with each other, a position of the reflective member, and an orientation of the reflective surface at which the excitation light reflected on the reflective surface enters the prism and impinges the specific position on the metal film when the reflective member is positioned at the position, and to perform the first positioning of the reflective member based on the table.

7. The surface plasmon resonance fluorescence analysis device according to claim 1, wherein
the reflective member is a dielectric multilayer mirror.

8. A surface plasmon resonance fluorescence analysis device for measuring fluorescence emitted by excitation of a fluorescent material labeled on a specimen by an electric field based on surface plasmon resonance, the surface plasmon resonance fluorescence analysis device comprising:
a prism having a metal film formed on a predetermined surface thereof;
a light source portion which emits excitation light for causing surface plasmon resonance on the metal film; and
an incident path adjusting portion which allows the excitation light to enter the prism by reflection of the excitation light emitted from the light source portion, wherein
the incident path adjusting portion includes a reflective member having a reflective surface formed thereon for reflecting the excitation light from the light source portion, and a driving portion for driving the reflective member, and
the driving portion is configured to change a position of the reflective member and to adjust an orientation of the reflective surface in such a manner that the excitation light entered the prism is reflected at a specific position on the metal film.

9. The surface plasmon resonance fluorescence analysis device according to claim 8, further comprising:
a light measuring portion which is configured to measure an intensity of light to be generated on a side of the metal film opposite from a side of the prism by reflection of the excitation light on the metal film; and
a control portion which controls the driving portion and the light measuring portion, wherein
the control portion controls the driving portion to perform first positioning of the reflective member, the first positioning being such that the control portion controls the light measuring portion to measure the intensity of light to be generated on the opposite side of the metal film while changing an incident angle of the excitation light with respect to the metal film by controlling the driving portion to change the position of the reflective member and to adjust the orientation of the reflective surface, and thereafter, the control portion controls the driving portion so that the position of the reflective member and the orientation of the reflective surface respectively coincide with a position of the reflective member and with an orientation of the reflective surface when a maximum amount of light is detected by the light measuring portion.

10. The surface plasmon resonance fluorescence analysis device according to claim 9, wherein
the control portion performs a first scanning operation of measuring an intensity of light to be generated on the opposite side of the metal film at each respective incident angle while intermittently changing the incident angle in a first range, the first range being a range of the incident angles of the excitation light with respect to the metal film; and performs a second scanning operation of measuring an intensity of light to be generated on the opposite side of the metal film intermittently at an interval smaller than an interval of the incident angle in the first scanning operation, or performs a second scanning operation of measuring an intensity of light to be generated on the opposite side of the metal film while continuously changing the incident angle, in a second range to be defined based on a result of the first scanning operation, for obtaining the maximum amount of light, and the second range is included in the first range.

11. The surface plasmon resonance fluorescence analysis device according to claim 10, wherein the control portion is configured to store the second range with respect to a specific prism, and to obtain the maximum amount of light by performing the second scanning operation based on the stored second range, without performing the first scanning operation with respect to a prism other than the specific prism.

12. The surface plasmon resonance fluorescence analysis device according to claim 9, wherein the driving portion is configured to move the reflective member in a direction orthogonal to a reflection plane of the metal film where the excitation light is reflected, while maintaining the orientation of the reflective surface with respect to the metal film, and the control portion performs, after performing the first positioning, second positioning of the reflective member in the direction orthogonal to the reflection plane based on a measurement result obtained by controlling the driving portion to move the reflective member in the direction orthogonal to the reflection plane, and by controlling the light measuring portion to measure an intensity of light to be generated on the opposite side of the metal film.

13. The surface plasmon resonance fluorescence analysis device according to claim 9, wherein the control portion is configured to store, in a table in correlation with each other, a position of the reflective member, and an orientation of the reflective surface at which the excitation light reflected on the reflective surface enters the prism and impinges the specific position on the metal film when the reflective member is positioned at the position, and to perform the first positioning of the reflective member based on the table.

14. The surface plasmon resonance fluorescence analysis device according to claim 8, wherein the reflective member is a dielectric multilayer mirror.

15. A surface plasmon resonance fluorescence analysis method for measuring light emitted by excitation of a fluorescent material labeled on a specimen by an electric field based on surface plasmon resonance, the surface plasmon resonance fluorescence analysis method comprising:

a preparation step of preparing a prism having a metal film formed on a predetermined surface thereof, and of allowing a sample solution containing the specimen to flow on the metal film;

an excitation light emission step of emitting excitation light for causing surface plasmon resonance on the metal film;

a resonance angle scanning step of changing an incident angle of the excitation light with respect to the metal film while maintaining a state in which the excitation light that is reflected on a reflective surface of the reflective member and enters the prism is reflected at a specific position on the metal film, by changing a position of the reflective member having the reflective surface formed thereon for reflecting the excitation light, and by adjusting an orientation of the reflective surface, and of measuring an intensity of light to be generated on a side of the metal film opposite from a side of the prism by reflection of the excitation light on the metal film; and a positioning step of performing positioning of the reflective member in such a manner that the position of the reflective member and the orientation of the reflective surface respectively coincide with a position of the reflective member and with an orientation of the reflective surface when a maximum amount of light is measured in the scanning step.

* * * * *